(12) United States Patent
Chang et al.

(10) Patent No.: US 11,293,057 B2
(45) Date of Patent: Apr. 5, 2022

(54) AC ELECTROSPRAYED DROPLETS FOR DIGITAL AND EMULSION PCR

(71) Applicant: University of Notre Dame du Lac, South Bend, IN (US)

(72) Inventors: Hsueh-Chia Chang, South Bend, IN (US); David B. Go, South Bend, IN (US); Zdenek Slouka, South Bend, IN (US); Satyajyoti Senapati, South Bend, IN (US); Yongfan Men, South Bend, IN (US); Zehao Pan, South Bend, IN (US)

(73) Assignee: University of Notre Dame du Lac, South Bend, IN (US)

( * ) Notice: Subject to any disclaimer, the term of this patent is extended or adjusted under 35 U.S.C. 154(b) by 339 days.

(21) Appl. No.: 16/304,870

(22) PCT Filed: May 9, 2017

(86) PCT No.: PCT/US2017/031715
§ 371 (c)(1),
(2) Date: Nov. 27, 2018

(87) PCT Pub. No.: WO2017/209906
PCT Pub. Date: Dec. 7, 2017

(65) Prior Publication Data
US 2019/0352698 A1    Nov. 21, 2019

Related U.S. Application Data

(60) Provisional application No. 62/342,912, filed on May 28, 2016.

(51) Int. Cl.
*B01L 3/00* (2006.01)
*C12Q 1/00* (2006.01)
(Continued)

(52) U.S. Cl.
CPC .......... *C12Q 1/686* (2013.01); *B01L 3/50273* (2013.01); *B01L 3/502792* (2013.01); *C12Q 1/6851* (2013.01); *B01L 2200/10* (2013.01)

(58) Field of Classification Search
None
See application file for complete search history.

(56) References Cited

U.S. PATENT DOCUMENTS 7,247,338 B2    7/2007  Pui et al.
8,267,914 B1    9/2012  Chang et al.
(Continued)

OTHER PUBLICATIONS

Alberini et al., "Influence of DC Electric Field upon the Production of Oil-In-Water-In-Oil Double Emulsions in Upwards mm-Scale Channels at Low Electric Field Strength," Exp Therm Fluid Sci., 81:265-276, Feb. 2017.
(Continued)

*Primary Examiner* — Nathan A Bowers
(74) *Attorney, Agent, or Firm* — Haukaas Fortius PLLC; Michael H. Haukaas

(57) ABSTRACT

The invention provides an alternating current electrospray technology that can generate micron sized droplets in oil at very high throughput for emulsion or digital PCR (Polymerase Chain Reaction). This technology outperforms the throughput of the current gold standard in droplet generation using flow-focusing technology by at least a factor of 100. The design is simple and can generate a billion to a trillion monodispersed droplets in about one hour. This is much faster than flow-focusing which is limited to a few million droplets per hour. The droplet size and generation rate can also be easily adjusted by changing the voltage of the AC electric field. The range of produced droplet sizes is about 1-100 microns, wherein the droplets are monodispersed in size.

20 Claims, 12 Drawing Sheets

(51) Int. Cl.
  *C12Q 1/686* (2018.01)
  *C12Q 1/6851* (2018.01)

(56) References Cited

U.S. PATENT DOCUMENTS

| | | | |
|---|---|---|---|
| 8,273,573 | B2 | 9/2012 | Ismagilov et al. |
| 8,716,675 | B2 | 5/2014 | Chetwani et al. |
| 2002/0009727 | A1 | 1/2002 | Schultz et al. |
| 2002/0153621 | A1 | 10/2002 | Ganan-Calvo |
| 2008/0166793 | A1* | 7/2008 | Beer ............... B01L 3/502784 435/287.2 |
| 2009/0114090 | A1 | 5/2009 | Gu et al. |
| 2010/0155496 | A1 | 6/2010 | Stark et al. |
| 2012/0199732 | A1 | 8/2012 | Chetwani et al. |
| 2013/0017148 | A1 | 1/2013 | Larsen et al. |
| 2013/0109575 | A1* | 5/2013 | Kleinschmidt ........ G01N 1/38 506/2 |
| 2015/0157569 | A1 | 6/2015 | Shum et al. |
| 2016/0172178 | A1* | 6/2016 | Apffel ................ H01J 49/168 250/395 |
| 2017/0253915 | A1* | 9/2017 | Du ........................ B01J 2/06 |
| 2019/0006165 | A1* | 1/2019 | Corr ..................... H01J 49/165 |

OTHER PUBLICATIONS

Anna et al., "Formation of Dispersions using "Flow Focusing" in Microchannels," Appl. Phys. Lett., 82(3):364-366, Jan. 2003.
Baker, M., "Digital PCR Hits Its Stride," Nat Methods, 9:541-544, May 2012.
Castro-Hernandez et al., "AC Electrified Jets in a Flow-Focusing Device: Jet Length Scaling," Biomicrofluidics., 10(4):043504, Jun. 2016.
Chetwani et al., "High-Frequency AC Electrospray Ionization Source for Mass Spectrometry of Biomolecules," J Am Soc Mass Spectrom., 21(11):1852-1856, Nov. 2010.
Chetwani et al., "Universal Cone Angle of AC Electrosprays Due to Net Charge Entrainment," Phys Rev Lett., 101(20):204501; Nov. 2008.
Gu et al., "Controlled Drop Generation for Digital Microfluidic Systems by Means of Electrowetting," Proc. 14th International Conference on Micro Total Analysis Systems (MicroTas), pp. 1808-1810, Oct. 2010.
Hatch et al., "1-Million Droplet Array with Wide-field Fluorescence Imaging for Digital PCR," Lab Chip., 11(22):3838-3845, Nov. 2011.
International Search Report and Written Opinion of the ISA/US dated Sep. 28, 2017 in International Application No. PCT/US2010/031715; 11 pgs.
Maheshwari et al., "Anomalous Conical Menisci Under an AC Field-Departure from the DC Taylor Cone," Appl Phys Lett., 89(23):234103, Dec. 2006.
Maheshwari et al., "Assembly of Multi-Stranded Nanofiber Threads through AC Electrospinning," Adv. Mater., 21:349-354, Jan. 2009.
Nakano et al., "Single-Molecule PCR using Water-in-oil Emulsion," J Biotechnol., 102(2):117-124, Apr. 2003.
Tanaka et al., "Hands-Off Preparation of Monodisperse Emulsion Droplets Using a Poly(dimethylsiloxane) Microfluidic Chip for Droplet Digital PCR,"Anal. Chem., 87(8):41 34-4143, Mar. 2015.
Wang et al., "Electrospray Cone-Jet Breakup and Droplet Production for Electrolyte Solutions," Europhys Lett., 100(2):64003, Oct. 2012.
Yeo et al., "A New AC Electrospray Mechanism by Maxwell-Wagner Polarization and Capillary Resonance," Phys Rev Lett., 92(13):133902, Apr. 2004.
Zhang et al., "Digital Quantification of Mirna Directly in Plasma using Integrated Comprehensive Droplet Digital Detection," Lab Chip., 15(21):4217-4226, Nov. 2015.
Takei et al., "PCR under Low Ionic Concentration Buffer Conditions", Chemistry Select 2018, 3,973-976. DOI:10.1002/slct.201702542.

* cited by examiner

1. Positive
2. Negative (no template)
3. Positive
4. Negative (no template)
5. Positive
6. Negative (no PCR)

Original Photo        After Matlab Processing 10 droplets in frame        2 droplets in frame 1. Positive Control
2. Positive Control
3. 1mM CaCl$_2$
4. 100μM CaCl$_2$
5. 10μM CaCl$_2$
6. 1μM CaCl$_2$
7. 1/10 template concentration
8. Negative control

AC ELECTROSPRAYED DROPLETS FOR DIGITAL AND EMULSION PCR

RELATED APPLICATIONS

This application is a National Stage filing under 35 U.S.C. § 371 of International Application No. PCT/US2017/031715 filed May 9, 2017, which claims priority under 35 U.S.C. § 119(e) to U.S. Provisional Patent Application No. 62/342,912, filed May 28, 2016, which applications are incorporated herein by reference.

BACKGROUND OF THE INVENTION

Digital and Emulsion PCR is a commercialized technology that inserts one biopolymer of nucleic acids into a single droplet with the PCR cocktail for performing a Polymerase Chain Reaction (PCR) in the droplet. Whether each droplet contains the target nucleic acid (amplicon) is then determined by optical reporters, typically molecular beacons, during or after PCR amplification. The advantage of such nucleic acid isolation is that it minimizes cross-talk and incorrect amplification in a heterogeneous sample with many different nucleic acids of similar sequences. Digital PCR (dPCR) hence minimizes sample pretreatment considerably. It also allows enumeration of a small number of target nucleic acids. It is considered to be ideal for micro RNA (miRNA) profiling, a promising early diagnostic assay, which quantifies a small number of target miRNA out of more than a thousand others, each with only a few mismatches because of the short length (22 bases) of miRNAs. It is also suitable for cell-free protein engineering or directed evolution where a single sequence must be selected out of trillions of different permutations that can express the proper protein. However, the current emulsion or flow-focusing dPCR technology do not have a sufficiently high throughput to provide practical large scale screening for protein engineering, directed evolution, and other large-volume assays.

Digital PCR can be useful for early detection of cancer, which is important for maximizing chances of patient survival. Liquid biopsy is currently the preferred method of screening due to minimized invasiveness, reduced patient pain, and lower cost. In recent years, miRNA has received significant attention as the preferred biomolecule used for early cancer screening due to its expression level change in very early stages of cancer before symptoms are observed. In addition, miRNA is relatively stable inside blood compared to other RNAs.

Difficulties of accurate quantification and profiling of different miRNA include requirement of high dynamic range and high sensitivity. The throughput of current flow-focusing technologies cannot achieve both the high dynamic range and sensitivity needed to make the application of dPCR as a practical first option in diagnostic assays for cancer. Accordingly, there is a need for a technology that can reach the desirable throughput.

SUMMARY

Two of the most widely used technologies used for miRNA profiling are real-time PCR (qPCR) and digital PCR (dPCR). Each of those technologies are limited in one of the two areas: 1) qPCR has the large dynamic range required, but lacks the required sensitivity for rare miRNA, and 2) dPCR has very good sensitivity (at the level of single template detection), but lacks the dynamic range needed, due to the size and throughput of droplets generated. To fully utilize the high sensitivity of current dPCR technology while improving its dynamic range, a novel droplet generation method using an alternating current (AC) electrospray is disclosed. An integrated dPCR apparatus has been designed comprising a high production droplet generation unit, a PCR unit, and a detection unit (FIG. 1).

We have discovered that an AC spray can generate much more monodispersed droplets at micron dimensions because the droplets are weakly charged in comparison to other electrospray technologies. We also discovered that it is possible to AC spray a PCR cocktail and a nucleic acid sample into an oil to obtain droplets (FIG. 2) with a tunable radius, for example, between 1 to 10 microns (FIG. 3). Validation of PCR amplification has been carried out and compared to amplicons amplified without an AC electrospray step. Proper selection of surfactants, AC frequency, voltage and oil has produced a set of operating conditions that provide monodispersed droplets. An upper bound on the voltage and a lower bound on the droplet size was found beyond which the nucleic acid is denatured and cannot be amplified by PCR. The droplet size is a function of the voltage and frequency and the size dispersity is associated to the occurrence of a jet in front of the cone. Theses droplets can be tuned, for example, from one to 50 microns and are highly monodispersed (FIG. 3). More importantly, it has a throughput that is at least 100 times higher than the current flow-focusing state of the art. The droplets can also be generated with a very simple apparatus that requires no meticulous tuning (FIG. 4 and FIG. 5).

An AC electrospray of water drops in oil can reach at least a lower limit of 1-micron in droplet size for PCR amplification. However, it is also possible to spray other liquids, for example, oil-in-water, organic solvent-in-water, or organic solvent-in-oil etc., that can provide droplets at the nanoscale size. Such a nano-emulsion could be of interest to drug companies because a nano-emulsion is very stable and hence can deliver liquid drugs. A nano-emulsion can also be used for making soft material (i.e., from polymers and gels) drug encapsulations at the nanoscale.

Obtained experimental results indicate that droplets ranging from 1-5 μm can be generated using AC electrospray at the rate of 1 million drops per second, which is 30 times faster than currently available commercial products. The droplets are PCR viable and fluorescent signals can be detected using a CCD camera. About 70% of all templates can be detected using the disclosed, which can be improved with further optimization. In addition, AC electrospray dPCR is also more tolerant to presence of PCR inhibitors, which indicates less pretreatment will be required before the sample can be used for testing.

Accordingly, this disclosure provides an apparatus that can produce monodispersed droplets at an unprecedented rate. For example, an apparatus for a current droplet generator comprises a) an electrospray emitter having a conical end and an orifice at the conical end, and a conduit to the orifice for a pressurized fluid, wherein the emitter can generate liquid droplets from the pressurized fluid at the orifice by an alternating current; b) an alternating current electrode and an optional counter electrode that are configured to provide the alternating current; and c) a droplet chamber having one or more inlets for the electrospray emitter and a droplet suspending medium, wherein the conical end of the emitter is at least partially inserted into the chamber, and when the droplet suspending medium flows into the chamber the conical end is immersed in the medium; wherein more than 100 monodispersed liquid droplets per second can be produced from the pressurized fluid by the alternating current droplet generator in the droplet suspending medium to form an emulsion.

An embodiment of the above disclosed apparatus can be utilized in a droplet digital polymerase chain reaction (PCR) apparatus comprising: a) the alternating current droplet generator; b) a capillary for a pressurized fluid sample comprising template molecules to flow from the capillary to the conduit of the electrospray emitter; c) a PCR thermal cycler, having an optional Peltier heater, configured to receive an emulsion of a fluid sample from the droplet chamber; and d) a detector; wherein a sufficient number of liquid droplets are generated from a pressurized fluid sample to achieve a binary distribution of template molecules among the droplets, when an alternating current is applied to the pressurized fluid sample comprising template molecules at the electrospray emitter, and the distribution of zero or one template molecule per droplet is independent of the template number in the fluid sample.

This disclosure also provides a method for producing monodispersed droplets at an unprecedented rate. The method comprises: a) applying an alternating current electric field to an electrospray emitter; b) introducing a fluid into the emitter; and c) generating an electrospray by the emitter from the fluid at a rate of more than 100 liquid droplets per second in a droplet suspending medium to form a stable emulsion; wherein the electrospray produces monodispersed liquid droplets having a diameter ranging from about 0.1 micrometers to about 1000 micrometers in the droplet suspending medium.

An embodiment of the above method can be utilized in a method for performing a droplet digital polymerase chain reaction (PCR) comprising: a) applying an alternating current electric field to an electrospray emitter; b) introducing a fluid into the emitter, wherein the fluid comprises one or more template molecules and PCR reagents; c) generating an electrospray by the emitter from the fluid at a rate of more than 100 liquid droplets per second in a droplet suspending medium to form a stable emulsion; d) amplifying an amplicon of one or more template molecules in a PCR thermal cycler; and e) detecting the amplicons; wherein the electrospray produces monodispersed liquid droplets having a diameter ranging from about 0.1 micrometers to about 1000 micrometers in the droplet suspending medium.

BRIEF DESCRIPTION OF THE DRAWINGS

The following drawings form part of the specification and are included to further demonstrate certain embodiments or various aspects of the invention. In some instances, embodiments of the invention can be best understood by referring to the accompanying drawings in combination with the detailed description presented herein. The description and accompanying drawings may highlight a certain specific example, or a certain aspect of the invention. However, one skilled in the art will understand that portions of the example or aspect may be used in combination with other examples or aspects of the invention.

DETAILED DESCRIPTION

Figure 1:
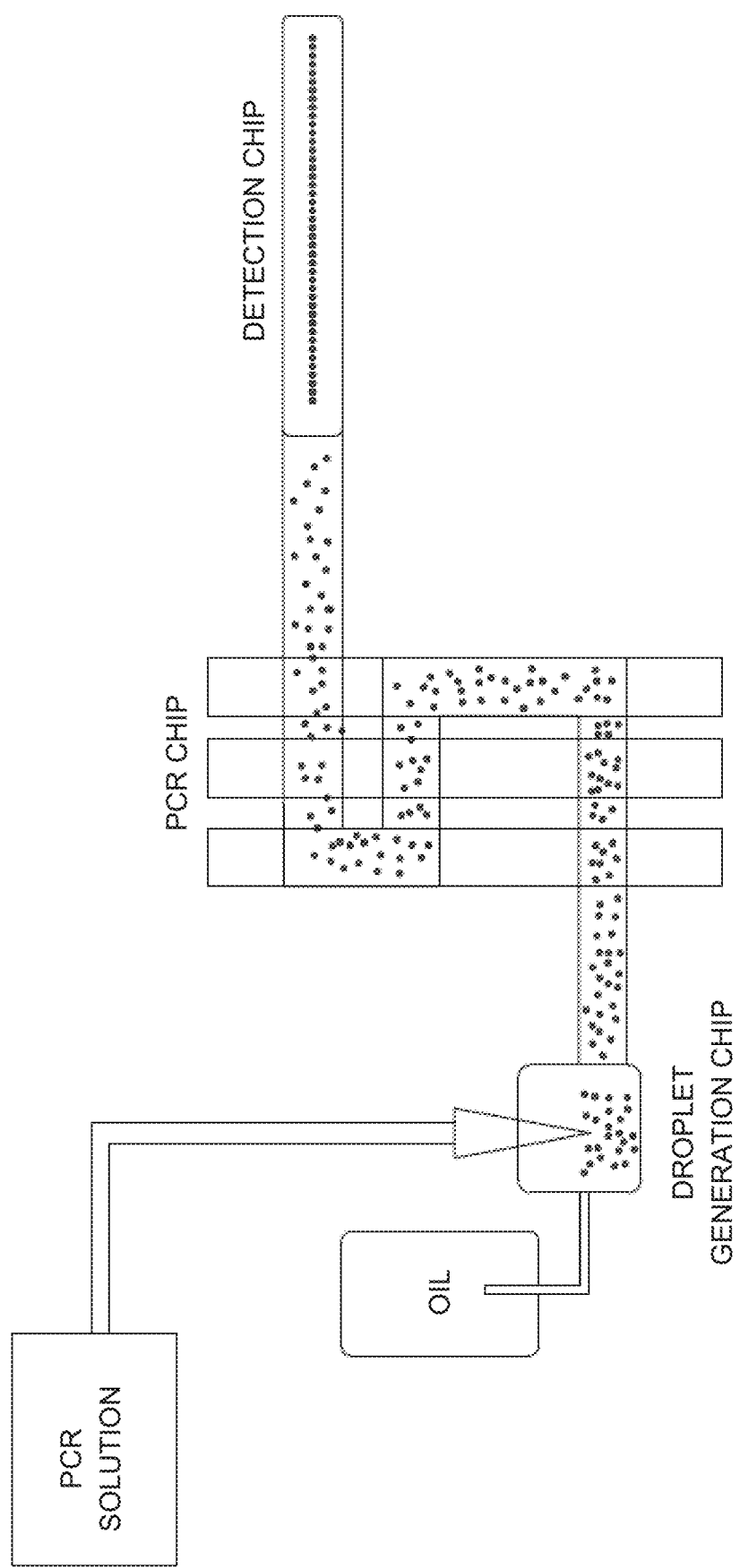
FIG. 1. Schematic of the AC spray digital PCR platform. It is divided into three sections: droplet generation, amplification, and detection.

Digital droplet PCR offers the ability to count target nucleic acids at one molecule resolution (Baker, *Nature* 2012, 9(6), 541). The current Digital PCR technology usually uses flow-focusing (Anna et al., *App. Phys. Letters* 2003, 82(3), 364; Zhang et al., *Lab Chip* 2015, 15, 4217), T-junction (Tanaka et al., *Analytical Chemistry* 2015, 15, 4217), or a hybrid version of flow-focusing and T-junction technologies (Hatch et al., *Lab Chip* 2011, 11, 3838). These droplet generation technologies use only hydrodynamic forces, such as shear and pressure. This technology can generate up to $10^5$ droplets per sample, after about 15 minutes. For example, the latest RainDance commercial product can generate up to 10 million droplets per sample, after 15 minutes (Baker, *Nature* 2012, 9(6), 541). The RainDance instrument price tag is substantial and the cost per sample is high. It is also difficult to tune the flow focusing and T-junction technologies to vary the droplet size and their rate of generation, because the balance among shear, capillary and pressure forces is delicate.

Easy tuning and the ability to generate droplets at a high rate are important for droplet digital PCR of one or more targets in a sample. The target can be a polynucleotide, and the target number is unknown in the original sample, i.e., the number of targets in the sample is unknown. With a large target number, it is necessary to generate significantly more droplets than targets (Baker, *Nature* 2012, 9(6), 541) such that there is either one target or no target in each droplet. However, better imaging and quantification accuracy is achieved with lower droplet number. Hence, for samples with a low target count, the platform would ideally allow for simple parameter adjustment to lower droplet generation rates. Currently, the flow-focusing and T-junction droplet digital PCR technologies typically partition an unknown sample into samples with different dilutions. They are tested repeatedly until the one sample with target number lower than the droplet number is found. These iterative dilution steps require more assay steps. The also lead to analyte loss as the assayed samples cannot be reused.

In this disclosure, a new AC spray technology for droplet generation uses an AC field instead of hydrodynamic forces, to pinch off the droplets at an emitter. This technology can generate up to $10^5$ drops per second or 100 million droplets, over a typical assay time of 15 minutes, with lower instrumentation and sample costs than other technologies discussed above. The droplet size and generation frequency can be easily tuned by adjusting the AC field and frequency for different samples with different target numbers for various applications.

Definitions

The following definitions are included to provide a clear and consistent understanding of the specification and claims. As used herein, the recited terms have the following meanings. All other terms and phrases used in this specification have their ordinary meanings as one of skill in the art would understand. Such ordinary meanings may be obtained by reference to technical dictionaries, such as *Hawley's Condensed Chemical Dictionary* 14$^{th}$ Edition, by R. J. Lewis, John Wiley & Sons, New York, N.Y., 2001.

References in the specification to "one embodiment", "an embodiment", etc., indicate that the embodiment described may include a particular aspect, feature, structure, moiety, or characteristic, but not every embodiment necessarily includes that aspect, feature, structure, moiety, or characteristic. Moreover, such phrases may, but do not necessarily, refer to the same embodiment referred to in other portions of the specification. Further, when a particular aspect, feature, structure, moiety, or characteristic is described in connection with an embodiment, it is within the knowledge of one skilled in the art to affect or connect such aspect, feature, structure, moiety, or characteristic with other embodiments, whether or not explicitly described.

The singular forms "a," "an," and "the" include plural reference unless the context clearly dictates otherwise. Thus, for example, a reference to "a compound" includes a plurality of such compounds, so that a compound X includes a plurality of compounds X. It is further noted that the claims may be drafted to exclude any optional element. As such, this statement is intended to serve as antecedent basis for the use of exclusive terminology, such as "solely," "only," and the like, in connection with any element described herein, and/or the recitation of claim elements or use of "negative" limitations.

The term "and/or" means any one of the items, any combination of the items, or all of the items with which this term is associated. The phrases "one or more" and "at least one" are readily understood by one of skill in the art, particularly when read in context of its usage. For example, the phrase can mean one, two, three, four, five, six, ten, 100, or any upper limit approximately 10, 100, or 1000 times higher than a recited lower limit. For example, one or more template molecules refers to one to fifty, one to forty, one to thirty, etc., for a sample containing any number of template molecules.

As will be understood by the skilled artisan, all numbers, including those expressing quantities of ingredients, flow rates, or sample numbers, and properties such as molecular weight, reaction conditions, voltages, electric currents, and so forth, are approximations and are understood as being optionally modified in all instances by the term "about." These values can vary depending upon the desired properties sought to be obtained by those skilled in the art utilizing the teachings of the descriptions herein. It is also understood that such values inherently contain variability necessarily resulting from the standard deviations found in their respective testing measurements. When values are expressed as approximations, by use of the antecedent "about," it will be understood that the particular value without the modifier "about" also forms a further aspect.

The terms "about" and "approximately" are used interchangeably. Both terms can refer to a variation of ±5%, ±10%, ±20%, or ±25% of the value specified. For example, "about 50" percent can in some embodiments carry a variation from 45 to 55 percent, or as otherwise defined by a particular claim. For integer ranges, the term "about" can include one or two integers greater than and/or less than a recited integer at each end of the range. Unless indicated otherwise herein, the terms "about" and "approximately" are intended to include values, e.g., weight percentages, proximate to the recited range that are equivalent in terms of the functionality of the individual ingredient, composition, or embodiment. The terms "about" and "approximately" can also modify the end-points of a recited range as discussed above in this paragraph.

As will be understood by one skilled in the art, for any and all purposes, particularly in terms of providing a written description, all ranges recited herein also encompass any and all possible sub-ranges and combinations of sub-ranges thereof, as well as the individual values making up the range, particularly integer values. It is therefore understood that each unit between two particular units are also disclosed. For example, if 10 to 15 is disclosed, then 11, 12, 13, and 14 are also disclosed, individually, and as part of a range. A recited range (e.g., weight percentages, carbon groups, polymer sizes) includes each specific value, integer, decimal, or identity within the range. Any listed range can be easily recognized as sufficiently describing and enabling the same range being broken down into at least equal halves, thirds, quarters, fifths, or tenths. As a non-limiting example, each range discussed herein can be readily broken down into a lower third, middle third and upper third, etc. As will also be understood by one skilled in the art, all language such as "up to", "at least", "greater than", "less than", "more than", "or more", and the like, include the number recited and such terms refer to ranges that can be subsequently broken down into sub-ranges as discussed above. In the same manner, all ratios recited herein also include all sub-ratios falling within the broader ratio. Accordingly, specific values recited for radicals, substituents, and ranges, are for illustration only; they do not exclude other defined values or other values within defined ranges for radicals and substituents. It will be further understood that the endpoints of each of the ranges are significant both in relation to the other endpoint, and independently of the other endpoint.

One skilled in the art will also readily recognize that where members are grouped together in a common manner, such as in a Markush group, the invention encompasses not only the entire group listed as a whole, but each member of the group individually and all possible subgroups of the main group. Additionally, for all purposes, the invention encompasses not only the main group, but also the main group absent one or more of the group members. The invention therefore envisages the explicit exclusion of any one or more of members of a recited group. Accordingly, provisos may apply to any of the disclosed categories or embodiments whereby any one or more of the recited elements, species, or embodiments, may be excluded from such categories or embodiments, for example, for use in an explicit negative limitation.

The term "contacting" refers to the act of touching, making contact, or of bringing to immediate or close proximity, including at the cellular or molecular level, for example, to bring about a physiological reaction, a chemical reaction, or a physical change, e.g., in a solution, in a reaction mixture, in vitro, or in vivo.

The term "substantially", as used herein, is a broad term and is used in its ordinary sense, including, without limitation, being largely but not necessarily wholly that which is specified. For example, the term could refer to a numerical value that may not be 100% the full numerical value. The full numerical value may be less by about 1%, about 2%, about 3%, about 4%, about 5%, about 6%, about 7%, about 8%, about 9%, about 10%, about 15%, or about 20%.

The term "electrospray" refers to an apparatus that employs electricity to disperse a fluid (i.e., a liquid) into liquid droplets, or a fine aerosol. High voltage is applied to a liquid supplied through an "emitter" constructed of a glass capillary or metallic capillary. The tip of the emitter can be, for example, tapered to have a conical shape with an orifice or opening at the front of the tip. For example, a Hamilton® micro-needle can serve as an emitter. The inner diameter of the micro-needle can be, for example, in the range of about 0.05 mm to about 0.5 mm. High voltage which produces the electrospray can be from a direct current (DC) electric field, or an alternating current (AC) electric field. The electrospray emitter can be "configured", for example, with an AC electrode in direct or indirect contact with the emitter. The electrode may also be inserted inside of, for example, a glass emitter. A liquid can be supplied, for example, through an inlet to the emitter by use of pressure. The pressure is applied, for example, through a manual syringe, a syringe pump, a diaphragm pump, a piston pump, a hydraulic pump, a compressed gas such as air or nitrogen, or any known apparatus or method of producing pressure, wherein the amount of pressure can be controlled, for example, by a pressure regulator.

The term "fluid", as used herein, refers to a liquid or a liquid mixture. The liquid can be, for example, water, an organic solvent, or an oil. The liquid can comprise a mixture of one or more miscible or immiscible liquids. The liquid can comprise a mixture of substances in the liquid, and the substances can be dissolved in the liquid, suspended in the liquid, or a combination thereof. The substances can include but are not limited to, for example, biological substances, proteins, DNA, RNA, enzymes, cells, various components of a cell, cancer cells, PCR reagents, surfactants, additives, salts, and oils. The fluid or the liquid can be in the form of a droplet, such as a liquid droplet or an aerosol produced by electrospray.

The term "droplet suspending medium (DSM)" refers to, for example, an oil, water, an organic solvent, which is immiscible with the fluid (defined above). The DSM is also immiscible with a liquid droplet, or an aerosol that is produced from a fluid, or immiscible with a liquid droplet, or an aerosol produced from an electrosprayed fluid.

The term "emulsion" refers to an immiscible mixture of liquid droplets and the droplet suspending medium, wherein the liquid droplets are "suspended" in the DSM. The suspended droplets that form an emulsion with the DSM can, for example, remain "stable" to the extent that the droplets do not "coalesce" to form larger droplets or form a liquid layer that partitions out of the DSM. The DSM can be, for example, an oil which "carries" an emulsion of liquid droplets from a chamber where the emulsion is produced to another chamber where a sample in the droplets is detected.

The term "immiscible" refers to liquids that do not form a homogeneous mixture when added together. For example, water is does not appreciably dissolve in an oil and therefore remains most separated from the oil. Similarly, water droplets suspended in an oil are immiscible with the oil which allow the water to remain as a droplet suspended in the oil.

The term "monodispersed" refers to two or more liquid droplets having substantially the same size, substantially the same diameter, substantially the same radius, or substantially a uniform size in dispersed phase. Monodispersed liquid droplets can vary in size by, for example, ±2 microns, ±5 microns, ±10 microns, or ±20 microns. When a range of monodispersed liquid droplets is recited, the range refers to the size of all droplets in the DSM, and not the different sizes of droplets in the DSM. For example, "monodispersed liquid droplets having a diameter ranging from about 0.1 micrometers to about 1000 micrometers in the droplet suspending medium" means, for a particular diameter of liquid droplet within the range cited, all the dispersed droplets have the same diameter, or a substantially similar diameter, for each of the droplet diameters in the range recited above.

The term "capillary" refers to a narrow bore tube that has an internal diameter of hair-like thinness, or an internal diameter of less than 5 mm, less than 4 mm, less than 3 mm, less than 2 mm, less than 1 mm, less than 0.5 mm, less than 0.25 mm, or less than 0.1 mm.

The term "metal" refers to a metal that conducts electricity and can comprise of, for example but not limited to steel, stainless steel, iron, titanium, aluminum, copper, platinum, tungsten, nickel, zinc, silver, gold, chromium, cobalt, iridium, lead, tin, palladium, cadmium, zirconium, vanadium, molybdenum, or combinations thereof.

The term "chamber" refers to a vessel that is partially or fully enclosed. The chamber may comprise, among other things, a fluid, a liquid, an oil, water, a mixture, an emulsion, a suspension, or one or more droplets. The chamber, for example, may hold a volume of a liquid, or oil, or an emulsion for a certain length of time or allow such fluids to pass or flow through the chamber. The chamber may be constructed of any material compatible with the fluid or liquid it carries. The chamber may have internal dimensions suitable for the purposes of, for example, where an electrospray forms and emulsion, where PCR thermal cycling takes place, or where a sample is detected. The chamber may be substantially two-dimensional or may be three dimensional, depending on the intended use of the chamber within the context of this disclosure. For example, a droplet chamber can comprise a cylindrical or a cubical volume with inlets and outlets for the production and flow of emulsions. A PCR chip can comprise of a single serpentine channel of continuous "S"-shaped loops, or an array of multiple channels. A chamber can be configured for batch PCR. A two-dimensional chamber may be used, for example, to detect the signal from a sample that is substantially along a plane, or a three-dimensional chamber may be used, for example, to collect samples for three-dimensional imaging using a three-dimensional detector.

The term "bodily fluid" refers to fluids inside living or deceased humans, animals, or plants. For example, in humans, a bodily fluid can be amniotic fluid, aqueous humour, vitreous humour, bile, blood serum, breast milk, cerebrospinal fluid, cerumen, chyle, chyme, endolymph, perilymph, exudates, feces, female ejaculate, gastric acid, gastric juice, lymph, mucus, pericardial fluid, peritoneal fluid, pleural fluid, pus, rheum, saliva, sebum, serous fluid, semen, smegma, sputum, synovial fluid, sweat, tears, urine, vaginal secretion, and vomit.

The term "biomarker" refers to a measurable indicator of some biological state or condition, or to a substance, the presence of which indicates the existence of a living organism. Life forms can shed unique chemicals, including DNA, or cancer miRNA into a surrounding area as evidence of their presence. Biomarkers can be measured and evaluated to examine normal biological processes, pathogenic processes, cancers, or pharmacologic responses to a therapeutic intervention.

The term "PCR reagent" is a term given ordinary meaning to a person skilled in the art and can include one or more PCR reagents. For example, a PCR reagent can comprise a polymerase enzyme (typically Taq Polymerase), primers, deoxynucleotide (dNTP), $MgCl_2$, cofactors, physiological buffers. For reverse-transcription, the PCR reagents can also comprise a reverse-transcription polymerase.

Embodiments of the Invention

In one embodiment of the disclosed apparatus, an alternating current droplet generator comprises: a) an electrospray emitter having a conical end and an orifice at the conical end, and a conduit to the orifice for a pressurized fluid, wherein the emitter can generate liquid droplets from the pressurized fluid at the orifice by an alternating current; b) an alternating current electrode and an optional counter electrode that are configured to provide the alternating current; and c) a droplet chamber having one or more inlets for the electrospray emitter and a droplet suspending medium, wherein the conical end of the emitter is at least partially inserted into the chamber, and when the droplet suspending medium flows into the chamber the conical end is immersed in the medium; wherein more than 100 monodispersed liquid droplets per second can be produced from the pressurized fluid by the alternating current droplet generator in the droplet suspending medium to form an emulsion.

Embodiments of the droplet chamber can include one inlet for both the electrospray emitter and the droplet suspending medium, or the droplet chamber can include two or more inlets, wherein the electrospray emitter and the droplet suspending medium enter the droplet chamber from separate inlets, wherein the inlets can be configured in different positions, for example, a T-junction (see FIG. 1). In other embodiments, one or more inlets may be pressurized, or one or more inlets may be pressurized at different time intervals.

In yet other embodiments of the alternating current droplet generator, the AC droplet generator may be grounded, the AC droplet generator may comprise a counter electrode, or the droplet chamber may comprise a counter electrode.

Embodiments of the emitter include an inner diameter in the range of about 0.01 mm to about 0.5 mm, about 0.01 mm to about 0.25 mm, about 0.01 mm to about 0.15 mm, about 0.05 mm to about 0.1 mm, about 0.1 mm to about 0.5 mm, about 0.0001 mm to about 0.1 mm, about 0.0001 mm to about 0.01 mm, or about 0.001 mm to about 0.01 mm. Embodiments of the orifice include a diameter in the range of about 50 nm to about 10000 nm, about 100 nm to about 10000 nm, about 250 nm to about 10000 nm, about 500 nm to about 10000 nm, about 750 nm to about 10000 nm, or about 1000 nm to about 10000 nm. Embodiments of an orifice shape can include a variety of shapes that are not limited to, for example, a conical shape, or a round shape.

Embodiments of the capillary include an inner diameter in the range of about 0.01 mm to about 2 mm, 0.01 mm to about 1 mm, 0.01 mm to about 0.5 mm, about 0.01 mm to about 0.25 mm, about 0.01 mm to about 0.15 mm, about 0.05 mm to about 0.1 mm, about 0.1 mm to about 0.5 mm, about 0.0001 mm to about 0.1 mm, about 0.0001 mm to about 0.01 mm, about 0.001 mm to about 0.01 mm, about 50 nm to about 10000 nm, about 100 nm to about 10000 nm, about 250 nm to about 10000 nm, about 500 nm to about 10000 nm, about 750 nm to about 10000 nm, or about 1000 nm to about 10000 nm.

Figure 4:
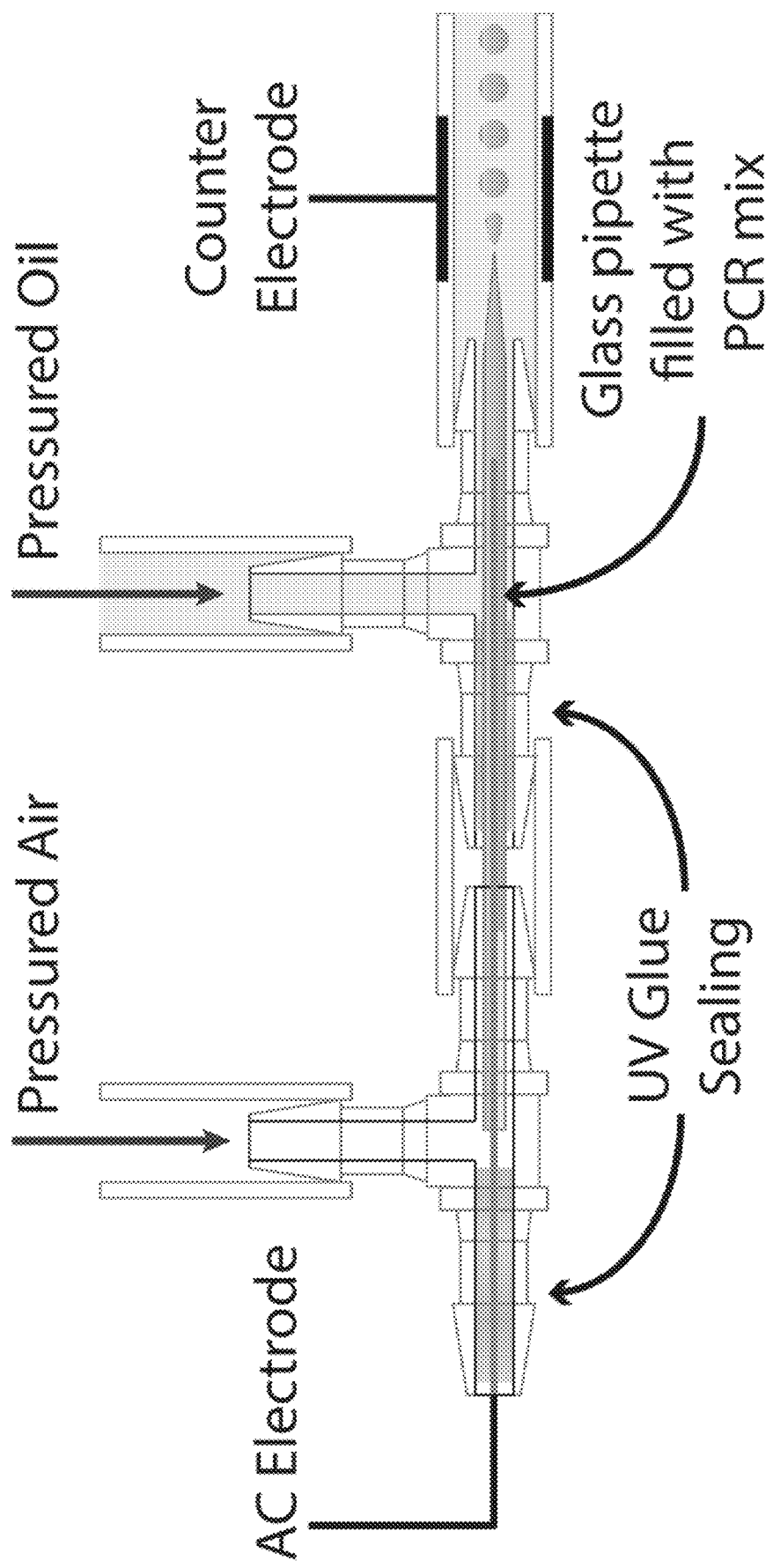
FIG. 4. Schematic diagram of alternating current droplet generator. The conical orifice has a diameter of about 1-10 microns. The capillary i.d. is about 100 microns, and capillary o.d. is about 1 mm.
Figure 5:
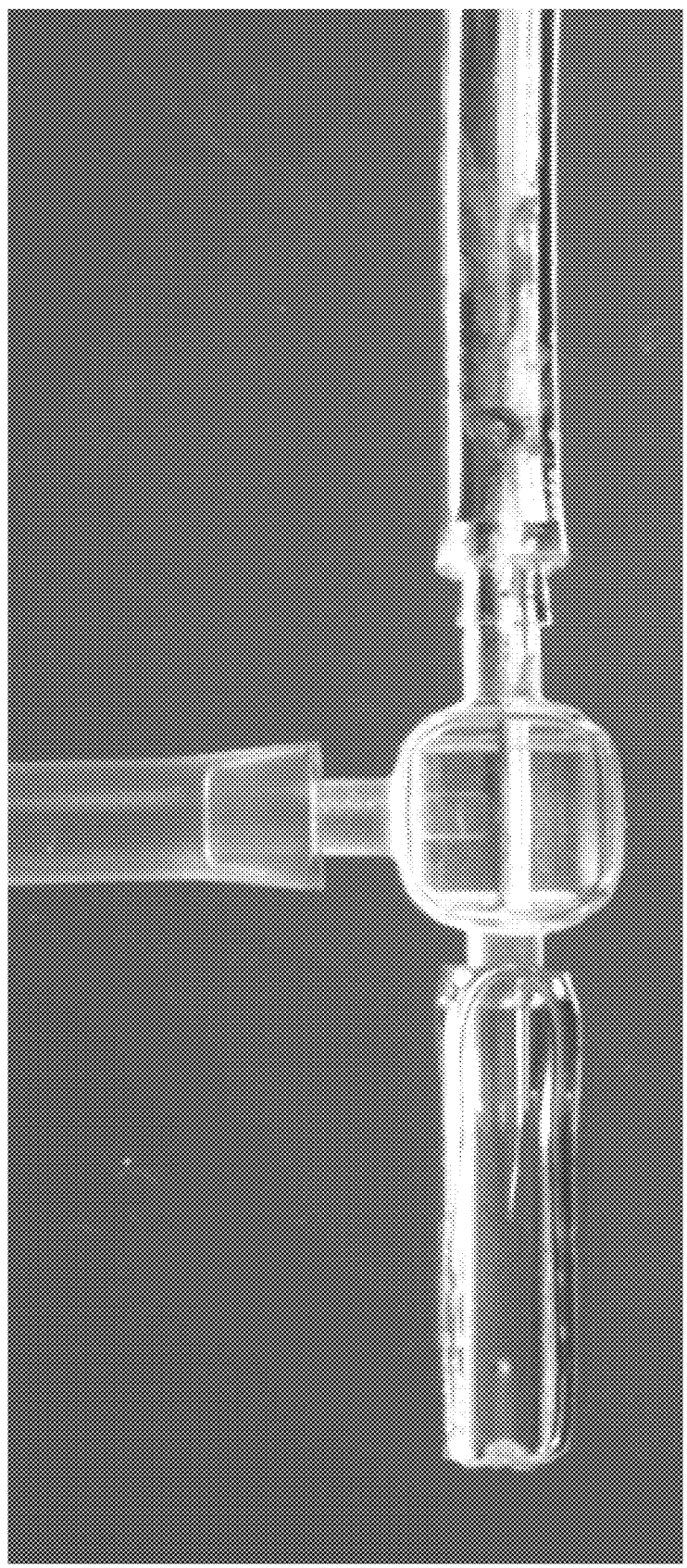
FIG. 5. Prototype apparatus of alternating current droplet generator.

In another embodiment, the electrospray emitter comprises an alternating current electrode, and a droplet chamber comprises a counter electrode and a droplet suspending medium. (for example, see FIG. 4). In additional embodiments, the droplet chamber is without a counter electrode and comprises a droplet suspending medium. In various embodiments of this disclosure the droplet suspending medium is an oil, wherein the oil may be at atmospheric pressure, the oil may be at a pressure that is higher than atmospheric pressure, or the oil may be at a pressure that is lower than atmospheric pressure.

In other embodiments, the oil may be flowing, or the oil may not be flowing. Embodiments of the oil flow rate include a flow rate ranging from about 0.01 milliliters per minute to about 100 milliliters per minute, about 0.1 milliliters per minute to about 50 milliliters per minute, or about 0.5 milliliters per minute to about 10 milliliters per minute.

In other embodiments, a droplet digital polymerase chain reaction (PCR) apparatus comprises: a) an alternating current droplet generator; b) a capillary for a pressurized fluid sample comprising template molecules to flow from the capillary to the conduit of the electrospray emitter; c) a PCR thermal cycler, having an optional Peltier heater, configured to receive an emulsion of a fluid sample from the droplet chamber; and d) a detector; wherein a sufficient number of liquid droplets are generated from a pressurized fluid sample to achieve a binary distribution of template molecules among the droplets, when an alternating current is applied to the pressurized fluid sample comprising template molecules at the electrospray emitter, and the distribution of zero or one template molecule per droplet is independent of the template number in the fluid sample.

Embodiments of the alternating current droplet generator include a rate of droplet generation of 100 droplets per second (dps), $10^3$ dps, $10^4$ dps, $10^5$ dps, $10^6$ dps, $10^7$ droplets per hour (dph), $10^8$ dph, or $10^9$ dph.

In additional embodiments, the electrospray emitter comprises glass with an internal alternating current electrode, or the electrospray emitter comprises a conductive metal in contact with an alternating current electrode.

In yet other embodiments, an emulsion can flow through the PCR thermal cycler, wherein the PCR thermal cycler comprises a) a serpentine channel, or b) a chip chamber for batch PCR.

In additional embodiments, the detector comprises a fluorescence detector, a radioactive detector, a two-dimensional detector, a three-dimensional detector, or a combination thereof.

In various other embodiments, the disclosed apparatus embodiments have a dynamic range of at least 4 orders of magnitude and a sensitivity to detect a polynucleotide of less than about 500 nucleic acid bases (NABs), less than about 100 NABs, less than about 50 NABs, or less than about 25 NABs.

Embodiments of the polynucleotide include DNA, genomic DNA, RNA, micro RNA (miRNA), messenger RNA (mRNA), transfer RNA (tRNA), ribosomal RNA (rRNA), small interfering RNA (siRNA).

In other additional embodiments, the disclosed apparatus embodiments have a sensitivity to detect micro ribonucleic acid (miRNA), ribonucleic acid (RNA), deoxyribonucleic acid (DNA), or a combination thereof.

One embodiment for a method for producing liquid droplets comprises: a) applying an alternating current electric field to an electrospray emitter; b) introducing a fluid into the emitter; and c) generating an electrospray by the emitter from the fluid at a rate of more than 100 liquid droplets per second in a droplet suspending medium to form a stable emulsion; wherein the electrospray produces monodispersed liquid droplets having a diameter ranging from about 0.1 micrometers to about 1000 micrometers in the droplet suspending medium.

Embodiments of monodispersed liquid droplets include droplet diameters ranging from about 0.1 micrometers to about 750 micrometers, about 0.1 micrometers to about 500 micrometers, about 0.1 micrometers to about 250 micrometers, about 0.1 micrometers to about 100 micrometers, about 0.1 micrometers to about 50 micrometers, about 0.1 micrometers to about 25 micrometers, about 0.1 micrometers to about 10 micrometers, about 0.1 micrometers to about 5 micrometers, about 0.1 micrometers to about 1 micrometer, or about 0.1 micrometers to about 0.5 micrometers.

Embodiments of monodispersed liquid droplets include droplet volumes of about 1 picoliter, about 2 picoliters, about 3 picoliters, about 4 picoliters, about 5 picoliters, about 10 picoliters, about 20 picoliters, about 50 picoliters, about 100 picoliters, about 200 picoliters, or about 500 picoliters.

In various embodiments, the diameter of a generated liquid droplet can be tuned to different diameters by varying the voltage of the electric filed. In other embodiments, the volume of a generated liquid droplet can be tuned to different volumes by varying the voltage of the electric filed. In yet other embodiments, the diameter of a generated liquid droplet can be tuned to different diameters by varying the frequency of the electric filed. In yet additional embodiments, the volume of a generated liquid droplet can be tuned to different volumes by varying the frequency of the electric filed.

In various embodiments of the disclosed methods, the frequency of the alternating current ranges from about 1 kilohertz to about 1000 kilohertz, about 10 kilohertz to about 500 kilohertz, about 25 kilohertz to about 250 kilohertz, or about 50 kilohertz to about 150 kilohertz. In various other embodiments, the potential of the alternating current ranges from about 0.01 kilovolts to about 1000 kilovolts, about 0.01 kilovolts to about 100 kilovolts, about 0.1 kilovolts to about 10 kilovolts, or about 0.1 kilovolts to about 1 kilovolts.

In yet other embodiments, the fluid comprises a template molecule, one or more PCR reagents, and water. In additional embodiments, the fluid further comprises a surfactant, b) the carrier oil further comprises a surfactant, or c) both the fluid and the carrier oil further comprise a surfactant. Other embodiments of surfactants comprise, but are not limited to, tween, fluorinated surfactants, sodium dodecyl sulfate, any commercially available surfactant, or any surfactant that helps prevent droplets from coalescing.

In yet other various embodiments, the fluid is flowing at rate of about 0.1 microliters per minute to about 10000 microliters per minute, about 1 microliters per minute to about 1000 microliters per minute, about 1 microliters per minute to about 100 microliters per minute, about 1 microliters per minute to about 75 microliters per minute, about 1 microliters per minute to about 50 microliters per minute, about 1 microliters per minute to about 25 microliters per minute, or about 1 microliters per minute to about 10 microliters per minute. In various embodiments, the fluid is maintained at a constant flow rate by constant pressure, or the fluid flows to the electrospray continuously at a constant flow rate, or the fluid flows to the electrospray continuously at a constant flow rate by constant pressure. In other embodiments, the fluid comprising water under pressure flows to the electrospray continuously.

In additional embodiments, the droplet suspending medium comprises a flowing carrier oil. In other embodiments, the carrier oil is a mineral oil, a fluorinated oil, a silicone oil, or a combination thereof. Embodiments of the carrier oil include a flow rate of about 10 microliters per minute to about 100 microliters per minute, about 1 microliters per minute to about 75 microliters per minute, about 1 microliters per minute to about 50 microliters per minute, about 1 microliters per minute to about 25 microliters per minute, or about 1 microliters per minute to about 10 microliters per minute.

In other various embodiments of the disclosed methods, the droplets to not substantially coalesce in the carrier oil. In additional; embodiments, the fluid comprises one or more biological substances. In yet other embodiments, the droplet suspending medium substantially comprises flowing water.

Various other embodiments of the disclosed methods include a method for performing droplet digital polymerase chain reaction (PCR) comprising: a) applying an alternating current electric field to an electrospray emitter; b) introducing a fluid into the emitter, wherein the fluid comprises one or more template molecules and PCR reagents; c) generating an electrospray by the emitter from the fluid at a rate of more than 100 liquid droplets per second in a droplet suspending medium to form a stable emulsion; d) amplifying an amplicon of one or more template molecules in a PCR thermal cycler; and e) detecting the amplicons; wherein the electrospray produces monodispersed liquid droplets having a diameter ranging from about 0.1 micrometers to about 1000 micrometers in the droplet suspending medium.

In other various embodiments, the amplicon detected is a polynucleotide of less than about 1000 nucleic acid bases (NABs), less than about 750 NABs, less than about 500 NABs, less than about 250 NABs, less than about 100 NABs, less than about 50 NABs, or less than about 25 NABs. In yet further embodiments, the polynucleotide comprises a micro-ribonucleic acid (miRNA), ribonucleic acid (RNA), deoxyribonucleic acid (DNA), or a combination thereof. In other embodiments, the polynucleotide comprises a biomarker for a disease, such as cancer.

Embodiments of diseases include, but are not limited to, cancer, infectious diseases (for example, malaria and dengue), diseases relating to drug addiction, heart diseases that can cause cardiac arrest, mental health diseases (causing, for example, depression), Alzheimer's disease, and immune diseases such as HIV. Embodiments of this disclosure are applicable for said aforementioned diseases comprising pathogenic DNA, mRNA, or host miRNA biomarkers, diseases comprising nuclei acid biomarkers, or other diseases comprising polynucleotide biomarkers.

In additional embodiments, the biomarker comprises a biomarker found in a bodily fluid. In other additional embodiments, the fluid further comprises a) a fluorescent reporter for PCR amplicons, b) a fluorescent reporter for multiplex target quantification, c) an optical barcode reporter for multiplex target quantification, or d) a radioactive reporter.

Technological Advances in Digital Droplet PCR and Applications

Cancer is the second most common cause of death in the United States, second to only cardiovascular diseases. The main reason behind this fact is that early stage cancer detection is difficult and symptoms are often detected only in Stage III and IV after metastasis has taken place. This is particularly true for cancers such as prostate cancer, with about a 28% 5-year survival rate when it is detected in late stages. Consequently, a biomarker that can be used as an indicator for early stages of cancer is essential for a favorable prognosis. In recent years, MicroRNA (miRNA) has started to receive significant attention for its role in cancer development. These are short (18-22 bases) single-stranded nucleotides that show different regulation patterns in cancer patients compared to healthy individuals. Thus, it is suggested that understanding miRNA expression and its mechanism of regulation is needed to monitor cancer progression. Furthermore, indication of a cancer disease can be revealed before any noticeable symptom emerges. Another advantage of studying miRNA is that due to their presence in biological fluids such as blood, urine, and saliva, it is possible to perform a liquid biopsy. MicroRNA and certain fragments of DNA that are shed by the tumors into the bloodstream can be used to screen for early-stage cancer. It can also explain cancer resistance, and used to monitor tumor response to treatment. The technique is a minimally invasive method compared to tissue biopsy, which is painful, expensive, and potentially risky for the patient. In contrast to messenger RNA (mRNA), miRNA is also very stable in vascular circulation and thus is ideal as a blood-based biomarker.

Two of the biggest challenges for detection and quantification of miRNA come from low template copy numbers inside body fluids and their change in expression levels, as different genes can be up-related or down-regulated across several orders of magnitude. For example, in pancreatic cancer, the miRNA, hsa-miR-492 was shown to be up-regulated by 2 to 3 orders of magnitude, while hsa-miR-217 is down-regulated by 2 to 3 orders of magnitude. In this case, a system with a dynamic range of 5 to 6 orders of magnitude is necessary to accurately profile such miRNAs. Specific strands of miRNA are also often rare in blood, ranging from 10 to 100 copies per millimeter of sample. Therefore, single-template sensitivity is often needed in to identify and quantify rare miRNAs.

Currently, polymerase chain reaction (PCR) is the most widely used method of amplifying low copy numbers of DNA across several orders of magnitude into large copies of a specific sequence. Real-time PCR (qPCR), which is currently the most widely used tool for miRNA profiling, is a technique based on PCR. This technique monitors amplification of DNA during PCR, in contrast to end-point detection used by conventional PCR in conjunction with gel electrophoresis. The biggest advantage of qPCR is its large dynamic range, which spans over 6 to 7 orders of magnitude and is a significant improvement over gel electrophoresis detection, which only has 1 to 2 orders of magnitude of dynamic range. However, qPCR suffers from several significant limitations. First, qPCR requires very pure samples since it will only work effectively under specific conditions, such as pH and ionic strength, and thus can often be inhibited by other ions and biomolecules. Consequently, samples from real body fluids often need to be extensively pretreated to remove interfering reagents, such as calcium ion ($Ca^{2+}$), bilirubin, and other proteins that are abundant in biological samples. The pretreatment process is often the most time-consuming and expensive step. Moreover, to accurately assess the expression level of a given miRNA, data must be compared to a previously-generated standard curve from the same template with identical primers and conditions. This additional process is both labor and time-consuming and susceptible to many uncertainties.

To overcome these limitations, a new PCR technique known as digital PCR (dPCR) was developed to provide a different approach to nucleic acid detection via amplification. In contrast to having a single bulk aqueous phase, the PCR solution is separated into individual droplets stabilized by surfactants inside an oil phase. The partitioning of the sample, which may need to be diluted, allows one to estimate the number of different molecules by assuming that the molecule population follows a Poisson distribution and that each droplet contains either 0 or 1 template of interest. DNA quantification is performed based on the number of total positive reactions. Since quantification is absolute and not compared to calibration curves, dPCR does not have a reliance on rate-based measurements (such as CT values), endogenous controls, and pre-constructed calibration curves. In addition, studies involving low copy numbers of nucleic acids have shown that digital PCR has a sensitivity and precision that is comparable to qPCR, and is able to detect a single DNA template inside a sample. One of the reasons is that, by partitioning different DNA templates inside individual droplets, the cross-talking between different templates have been minimized, thus reducing the probability of producing shorter, undesired amplicons. Since there the ratio of the number of target miRNA to the entire nucleic acid population is about $10^5$, isolating a maximum of $10^4$ targets from other nucleic acids in a typical 10-microliter sample would require $10^{10}$ droplets. This droplet number shall be used as the ideal number for a 10-microliter sample.

Similarly, it has been shown that dPCR displays a higher tolerance towards inhibitors in blood, urine, and saliva samples. The most common PCR inhibitor is $Ca^{+2}$, which can reach as high as 1 mM in many physiological samples. Protein inhibitors in blood can reach similar concentrations. If the number of droplets "p" greatly exceeds both the template number "m" and the inhibitor number "n", the probability of both being in the same droplet is $(mn/p^2)$. For a typical 10 microliter sample, the template number m does not exceed $10^4$ while the inhibitor number n is at most $10^{15}$ (corresponding to a maximum MN concentration). Hence, generating 5 micron droplets from the sample, or the equivalent ideal goal of $p=10^{10}$ droplets would reduce the probability of both inhibitor and template in the same droplet to less than 10%, or increase the PCR amplification efficiency by more than 10 times.

While digital PCR can improve upon several limitations attributed to qPCR, current techniques for droplet generation has imposed some challenges. With currently available technology, almost all droplets have been generated sequentially by flow focusing using Y junction microfluidic chips. The fastest droplet generation rate by this technique is about 30,000 droplets/second. The droplets generated are about 10-50 μm in diameter (about 1 picoliter per drop), While the sample is not diluted, dPCR suffers from a smaller dynamic range (4-5 orders of magnitude) compared to that of qPCR. With the current flow-focusing microfluidic technology, it would require about $10^7$ or several days to generate $10^{10}$ droplets, i.e., the ideal droplet number, to remove the effect of high-concentration inhibitors and to suppress interference. This problem can be improved with dilution, but it may reduce the copy number to below the detection limit, and throughput also becomes an issue with larger sample volume. Furthermore, there are several additional steps that must be performed between droplet generation and PCR amplification, which further increases sampling time and lowers the statistical accuracy for the quantification because of analyte loss during repeated handling.

Therefore, it is essential for a system with higher droplet production rate, smaller droplet size, and minimalized sample handling steps, to be developed. Here, this disclosure provides a novel droplet generation system using alternating current (AC) electrospray. The throughput of the disclosed. AC spray platform ($10^7$ per s) is 100 times higher than the current flow-focusing technology. It can offer the desirable $p=10^{10}$ droplet number, provide 100 times larger dynamic range and reduce inhibitor cross-talking even for high mM concentration inhibitors like $Ca^{+2}$ in a reasonable assay time of less than one hour, without or with minimum pretreatment. In this disclosure, an imaging technology suitable to quantify the number of fluorescent droplets for the described high throughput platform is significantly less costly than the single-droplet optical detection technology used for current digital PCR technologies. The disclosed AC spray and imaging system are connected by a continuous-flow loop PCR unit to allow high-throughput continuous operation that can assay multiple samples sequentially.

Alternating Current (AC) Electrospray Platform

Due to their limitations, neither current qPCR or dPCR technologies are ideal for accurate quantification of miRNA. Therefore, this disclosure provides the advantages of both systems while minimizing their shortcomings. Both DC and AC spray ionization methods are extensively used in mass spectrometry as a means of generating small, monodispersed droplets in air. AC electrospray is chosen for the purposes of this disclosure because it generates droplets with a desirable size (for example, 1-10 μm) that are weakly charged, making them more ideal for handling biological samples. In addition, it has been shown experimentally that a DC spray is very unstable when an aqueous phase is sprayed into oil, most likely due to an electric discharge into the oil phase. This instability is surmounted by employing an AC spray with a sufficiently high frequency so that the AC spray cone does not accumulate too much charge for a discharge to occur in the oil. By carefully controlling the parameters (frequency and voltage) of the electric field, stable droplets ranging from 1-5 μm can be generated at a much higher throughput (1 million droplets per second) than the existing digital PCR technology (limited to 30,000 drops per second), such that the ideal droplet number of $p=10^{10}$ can be reached in $10^3$ seconds or less than 1 hour. Furthermore, since the droplets generated by AC spray is much smaller (1-5 μm droplet size) than ones generated by traditional dPCR configured with Y-junction micro-channels (10-50 μm droplet size), a much larger number of droplets ($p=10^{10}$) can be generated from the same volume (10 microliter) of sample. This advance effectively increases the dynamic range by 2 to 3 orders of magnitude and reduces or eliminates the need for dilution. Lastly, to minimize sample handling time between droplet generation, amplification, and detection, a continuous flow and imaging system integrating the three processes have been designed and shown in FIG. 1.

The following Examples are intended to illustrate the above invention and should not be construed as to narrow its scope. One skilled in the art will readily recognize that the Examples suggest many other ways in which the invention could be practiced. It should be understood that numerous variations and modifications may be made while remaining within the scope of the invention.

EXAMPLES

General Methods

Figure 6:
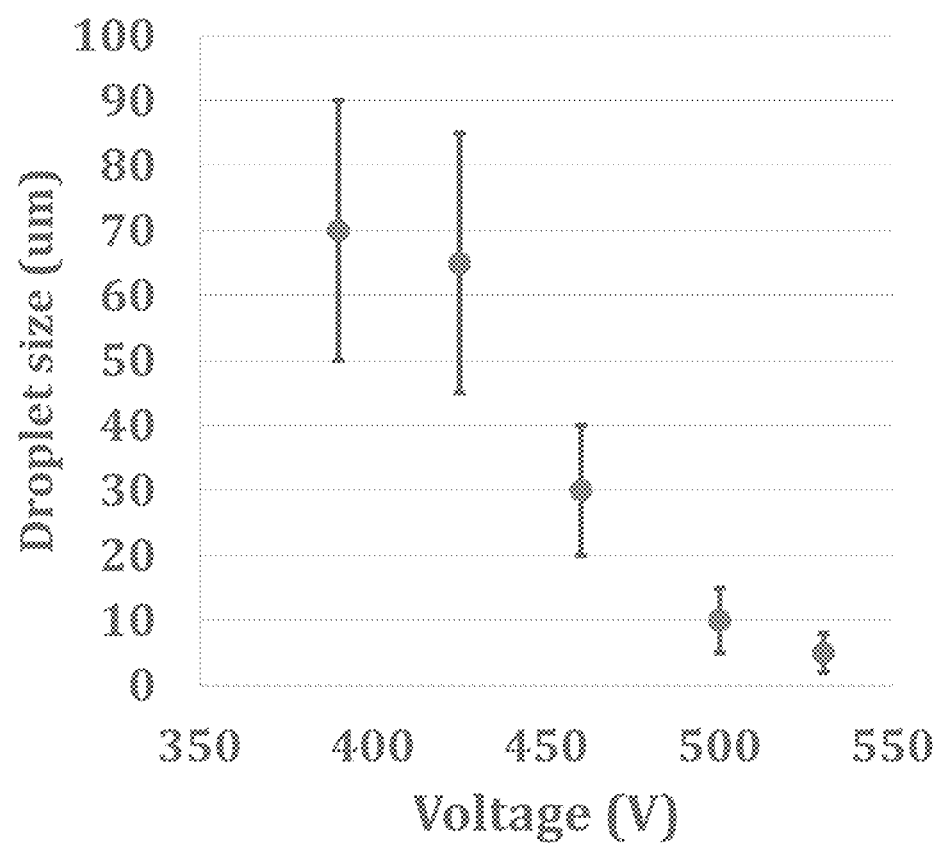
FIG. 6. Graph of droplet size as a function of voltage.
Figure 7:
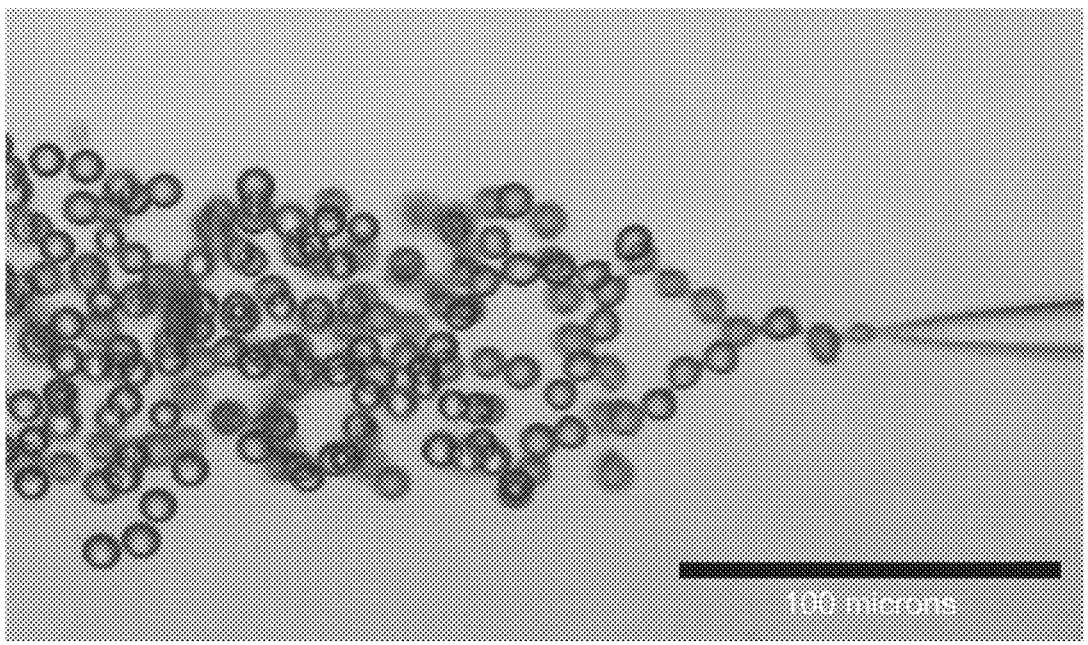
FIG. 7. Image for droplets at 460V (bar is 100 microns).
Figure 8:
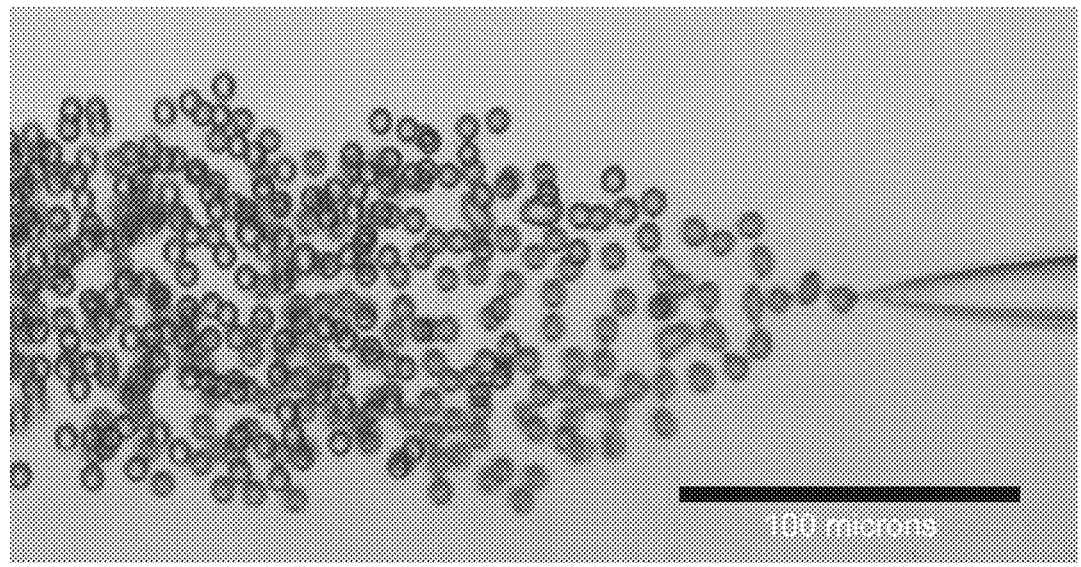
FIG. 8. Image for droplets at 500V (bar is 100 microns).

The disclosed invention can generate 100 to $10^5$ droplets per second. Droplet size can be tuned by adjusting the frequency (1 kHz to 1 MHz), the voltage (10 to 1000 V) and the water flow rate (10 microliter/min to 0.1 milliliter/min). The smaller the droplet the larger the generation rate. The graph in FIG. 6 shows how droplet size varies with voltage (FIG. 7 and FIG. 8). A sufficient number of droplets are generated for a given sample so that the droplets encapsulate either one or zero templates (e.g., a binary distribution of droplets).

Example 1. Generation of Stable Droplets Using AC Electrospray

Figure 2:
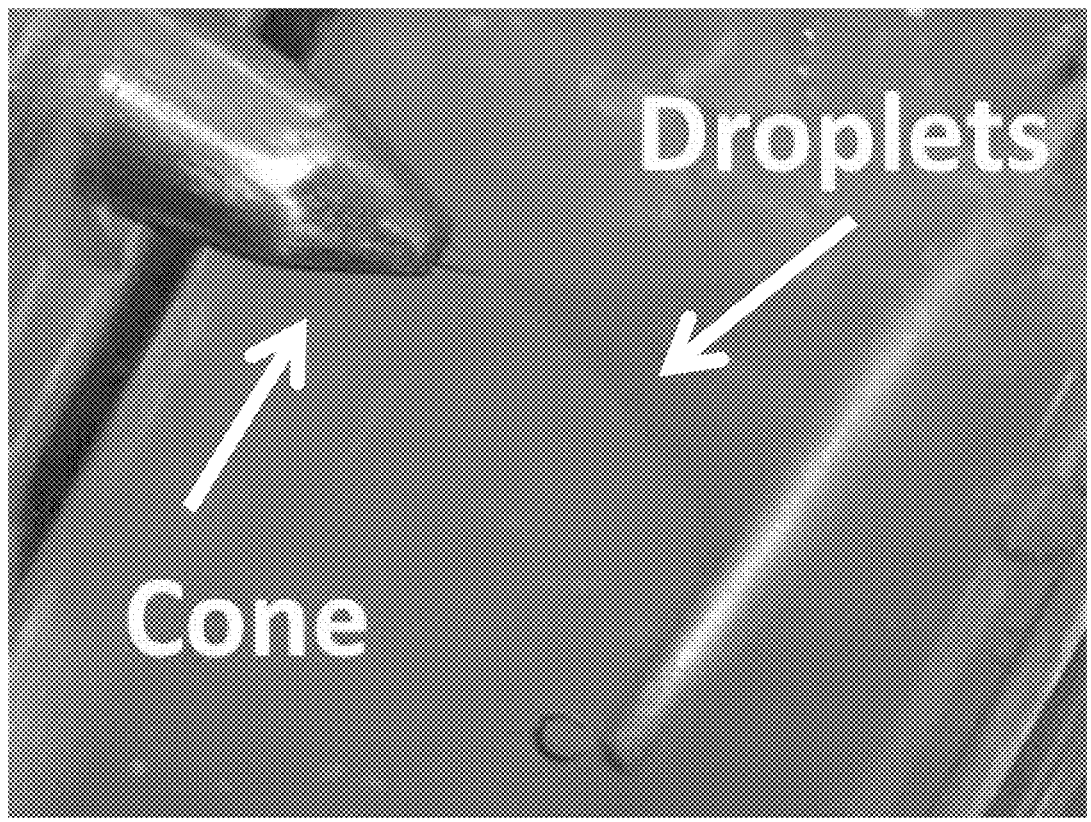
FIG. 2. Large-scale droplet generation inside mineral oil. The meniscus at the tip of the syringe is stretched into a conical shape by the electric field and disperses into droplets. The droplets appear as a very fine mist. In AC electrospray with PCR cocktail and nucleic acids, the mist at the end of the orifice comprises micron-sized water droplets with surfactants in the emulsion.
Figure 3:
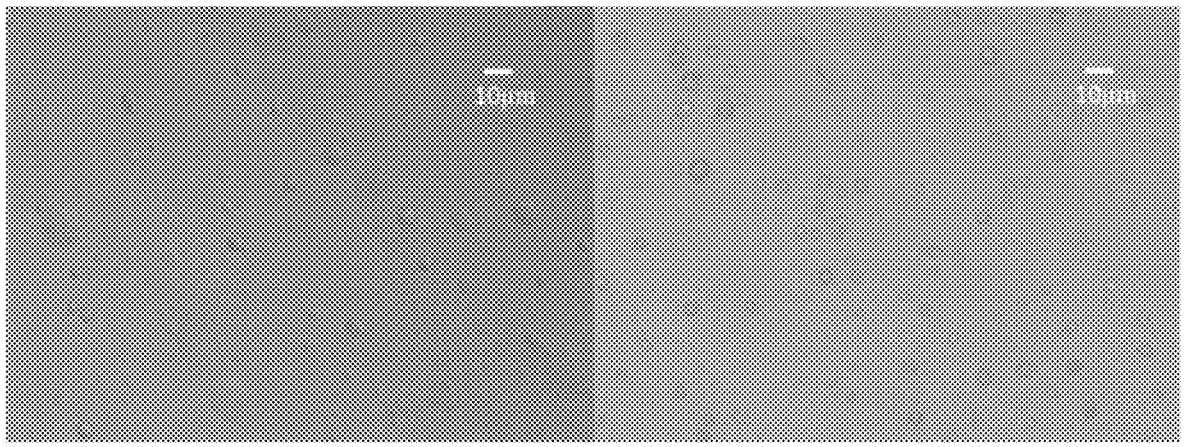
FIG. 3. Image of sprayed water drops in oil. Drops range between 1 to 10 microns. Droplets are stable before (left) and after (right) 2 hours of PCR.

An objective of this study is to identify the working regime of the AC spray at which droplets of desirable distribution can be obtained. It was determined experimentally that a frequency between 50 kHz and 150 kHz and a potential between 1.5 kV and 3.5 kV can be used to generate a stable AC cone inside oil (FIG. 2). Due to frequent and rapid change in temperature during PCR, droplets are often destabilized and coalescence into a bulk aqueous phase. Therefore, surfactants are needed to stabilize the droplets as well as to minimize surface tension so smaller droplets can be created. PCR buffer solution containing 8.5% Span 80 and 1.5% Brij-4 is used and droplets do not show coalescence after 30 cycles of PCR thermocycling (95° C. for 30 seconds, 59° C. for 45 seconds, 72° C. for 30 seconds), as shown in FIG. 3. While performing the experiment within the working regime of the experiment, it was observed that the size of the droplets did not appear to vary much with different frequency and potential, indicating that surfactant concentration might also be useful in controlling droplet size. The effect of surfactant and spray conditions on the droplet size will be further optimized.

Example 2. Affirmation of the Viability of PCR Reagents Inside Droplets

Figure 9:
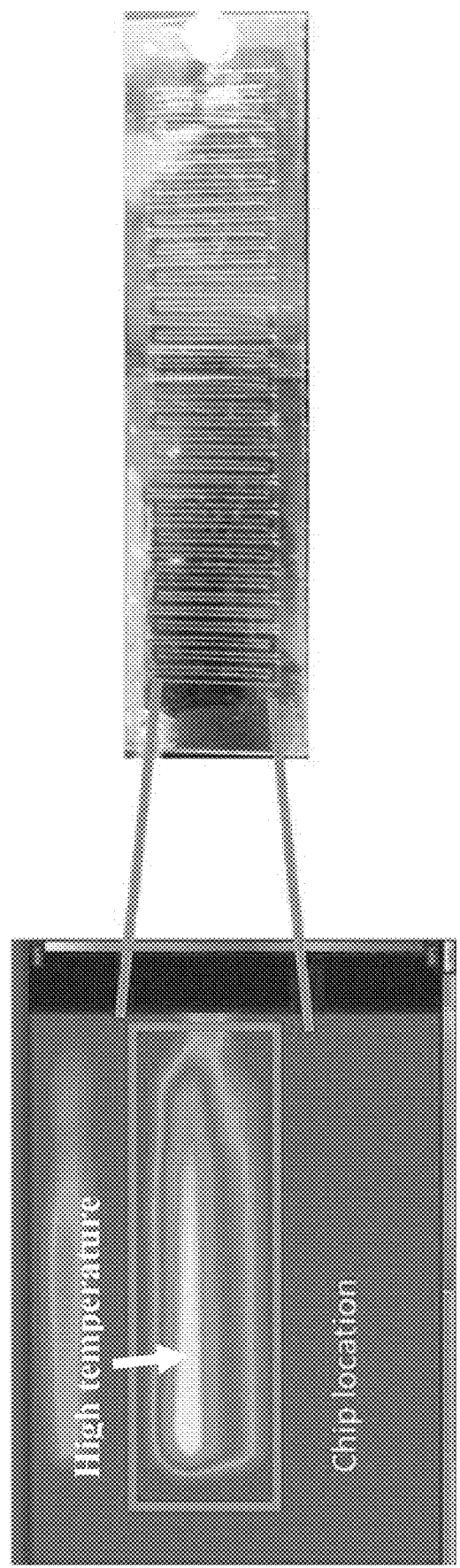
FIG. 9. Polycarbonate PCR chip and temperature profile when the chip is placed onto the Peltier heaters. Temperature gradient between 55° C. and 95° C. can be identified on the chip.
Figure 10:
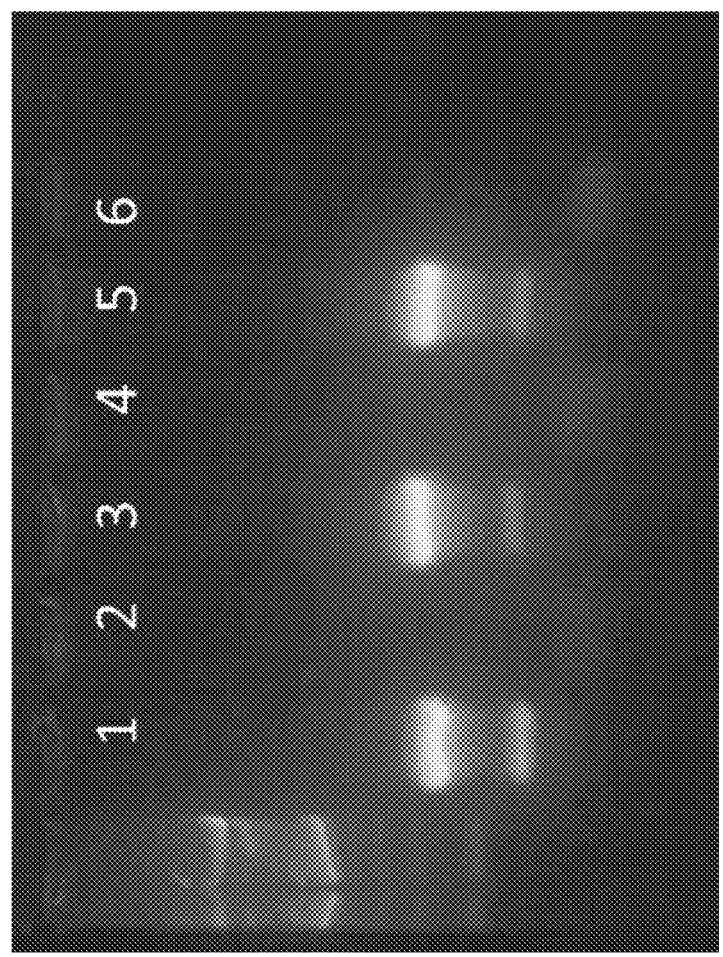
FIG. 10. PCR amplification inside loop-based PCR chip is successful. The correct amplicon is about 200 base pairs long. The nonspecific amplicon size is estimated to be 50-70 base pairs and is speculated to be primer dimers.

To affirm that the biological substances inside droplets that were generated from the electrospray retained their biological viability, the water-in-oil emulsions were subjected to PCR inside a serpentine PCR chip that was designed to immediately follow the droplet generation unit. A positive control using only aqueous PCR sample was also performed. The PCR chip was made from polycarbonate (1 mm×3 cm×150 μm) and mounted across Peltier heaters, one set at 95° C. and one set at 59° C. The dimensions of the chip are tuned based on the flow rate of the spray and oil, and each PCR cycle is designed to be between 30-40 seconds after accounting for the fact that TAQ polymerase works optimally between 70° C. and 80° C. and can amplify up to 100 bases per second at optimal temperature. It has been established that performing PCR at 2 to 3 static temperatures for extended periods of time is not necessary for low volume samples that can reach temperature equilibrium quickly and can be done with a temperature gradient as well. The amplicon of the PCR reaction is about 200 base pairs. A natural temperature gradient is created across the PCR chip (FIG. 9). Both aqueous positive control and emulsion samples are successfully amplified (FIG. 10) specifically by the continuous PCR chip. While no bands were observed in negative controls, two different bands were formed in positive sample targets, indicating that amplification is not completely specific and further tuning should eliminate the non-specific band. It is speculated that the shorter of the two bands is the result of primer dimer formation, which can be reduced by either increasing annealing temperature or reducing annealing time.

Figure 11:
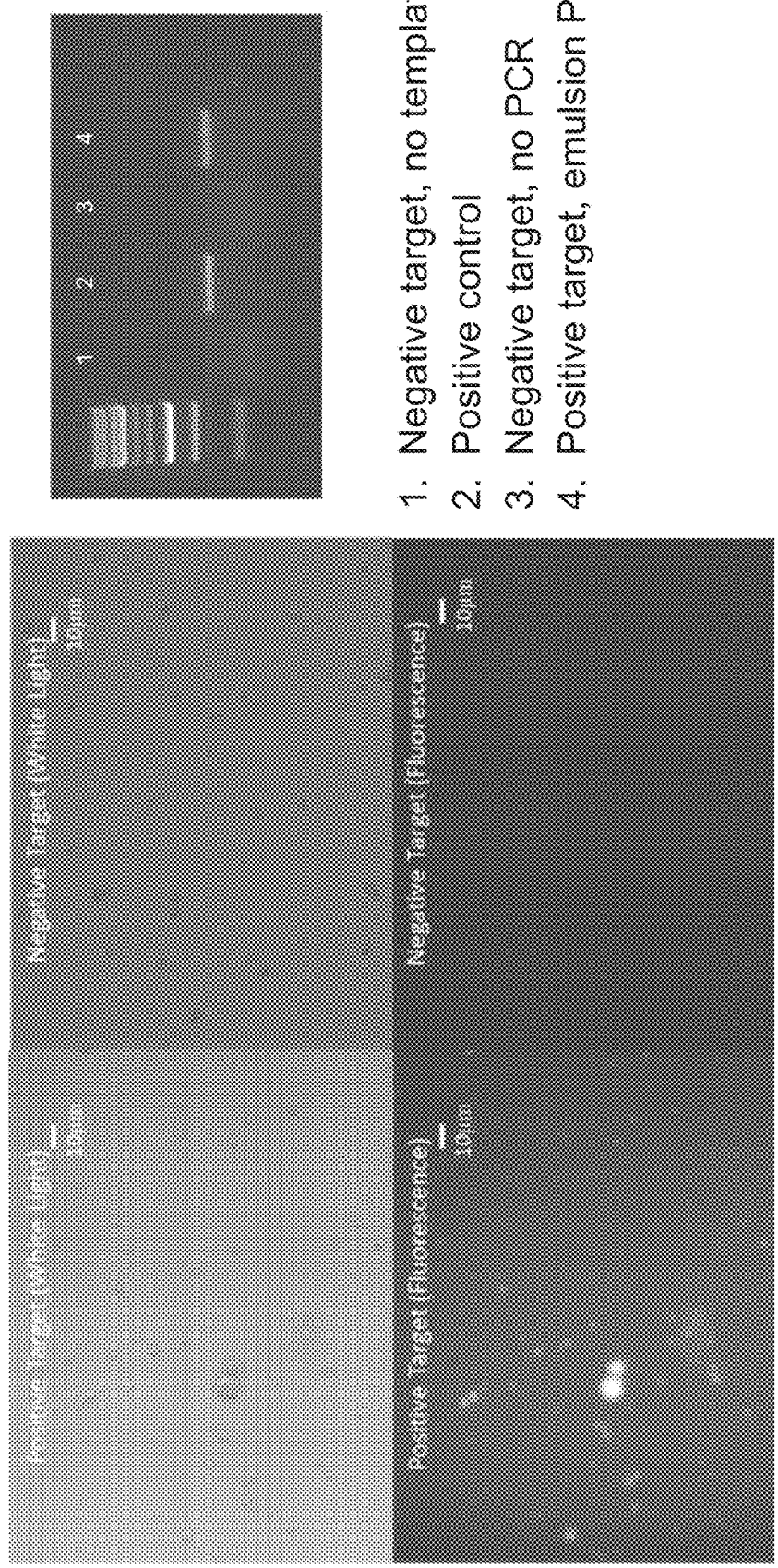
FIG. 11. PCR amplification is successful inside droplets and fluorescence signals can be detected. Gel electrophoresis is performed on the same samples for comparison.

Example 3. Development of a Fluorescent Detection Unit and an Analysis Program A component of the AC electrospray is the detection chip that is downstream of the PCR chip. The chip is placed under microscope using 20× magnification, and a CCD camera is used to capture the images of the droplets as they come in and exit the viewing window of the microscope. To match the upstream flow rate of the spray and PCR systems, the droplets will only have about 100 milliseconds of exposure time for fluorescence to be excited and detected. Therefore, a study was performed on 100 µM of fluorescence in PCR solution, mimicking the fluorescence intensity of PCR after 27 cycles. The solution was sprayed, which then flowed through the PCR chip, and subsequently collected in a 96-well plate for further studying. A very faint fluorescence can be detected, due to the short exposure time, which was enhanced by image processing to identify the droplets (FIG. 11). Thus, fluorescent droplets were successfully detected inside the 96-well plates.

Figure 12:
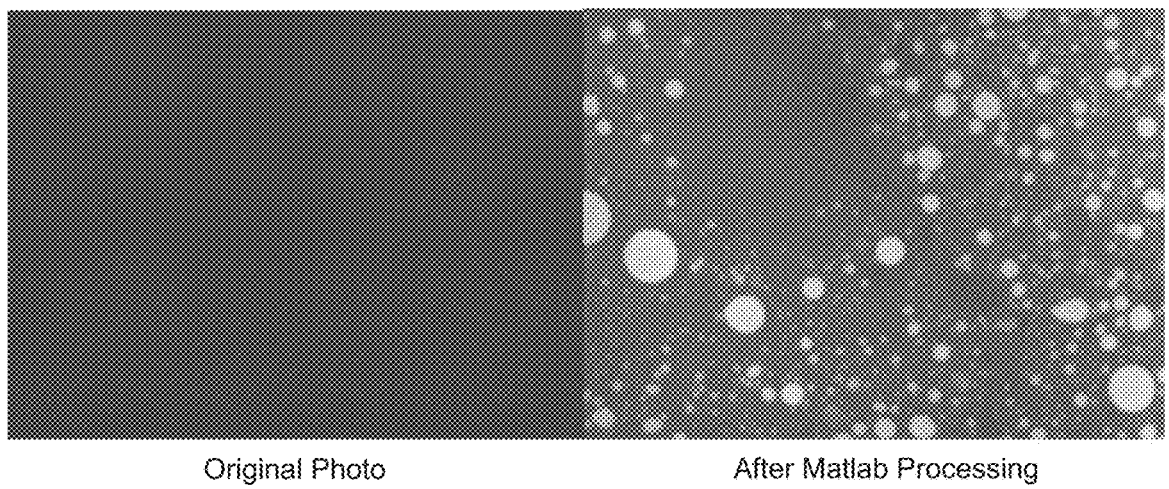
FIG. 12. Fluorescent droplets cannot be visually detected with unprocessed photo. Processed shows that fluorescent signal can be picked up by the camera at necessary exposure time of 100 ms or lower.
Figure 13:
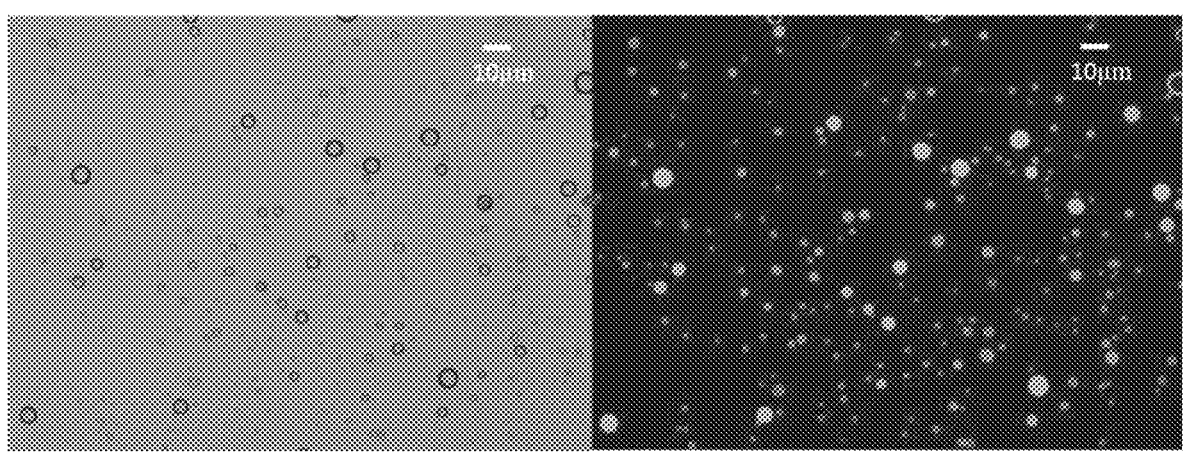
FIG. 13. Droplets can be identified under bright field or fluorescent light. Custom software made is able to identify and encircle (shown in green) droplets.

A glass chip was fabricated using hydrofluoric acid (HF) etching. The channel dimensions were 1 mm×3 cm×50 µm. Fluorescent droplets that were previous not visible before image processing could now be observed more ideally without image processing (FIG. 12). A thinner liquid layer due to the shallow depth of the channel results in less light dispersion. A software was developed having improvements that made it possible to automatically identify the droplets and perform a count of droplets (FIG. 13). Additional software can be added to the software to increase image processing speed by automation.

Example 4. Testing Integrated Continuous Flow Unit and Droplet Counting

Figure 14:
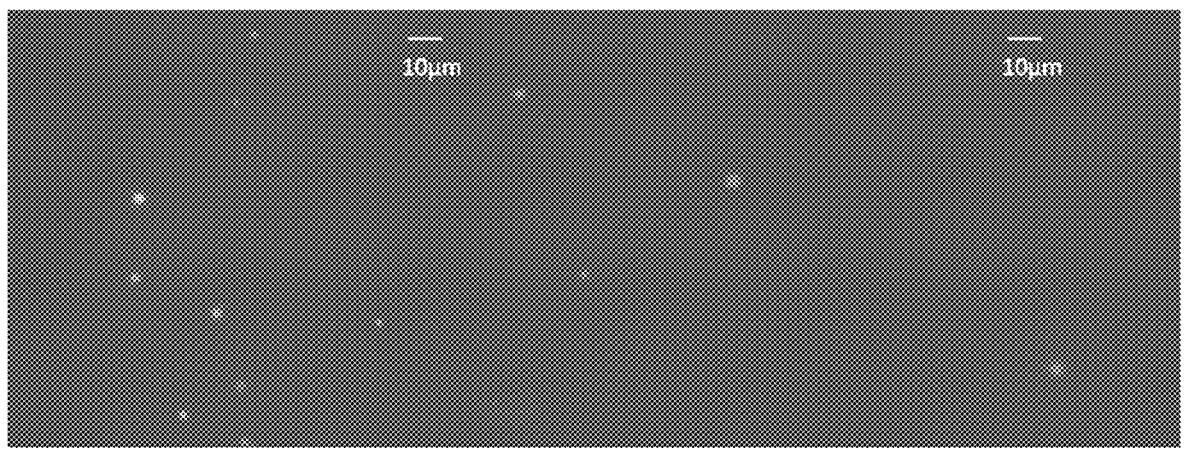
FIG. 14. Low number of droplets per frame (10 and 2) are successfully identified.

Above experiments individually demonstrated successful droplet generation, PCR amplification, and detection of fluorescent droplets in batch mode. The entire system from sample preparation to detection of fluorescent signals was then shown to be viable. Two flow streams were used in this experiment: the flow for a PCR solution was set at 2.5 µl/min and the flow of oil flow was set at 2.5 µl/min. The aqueous PCR solution was sprayed into the bulk oil and the oil-droplet mix flowed into the loop PCR chip for amplification. Regarding the detection chip, the lateral speed of the oil-droplet mixture was 1 cm/sec. Individual frames of snapshots were taken at a rate of 10 fps as the droplets enter and exit the viewing window of the microscope. Different concentrations of DNA templates were added to the PCR spray mixture. Images showing different numbers of fluorescent droplets are shown in FIG. 14. About 70% of theoretical had been detected for 100, 1000, and 10000 DNA copies inside the solution. This obtained percentage of theoretical could be due to factors from both amplification and detection steps. For amplification, due to the large number of droplets generated, it is possible that materials such as primer and polymerase which are used at lower concentration are not present in every single droplet. Hence, increasing the concentration of these materials may improve detection accuracy. As for detection chip, the channel was designed so that the droplets are mostly present in a monolayer, however, several fluorescent droplets identified tended to be out of focal plane which affected the number of droplets detected. This can be corrected.

Example 5. Comparison of Conventional PCR and AC dPCR with Inhibitors

Figure 15A:
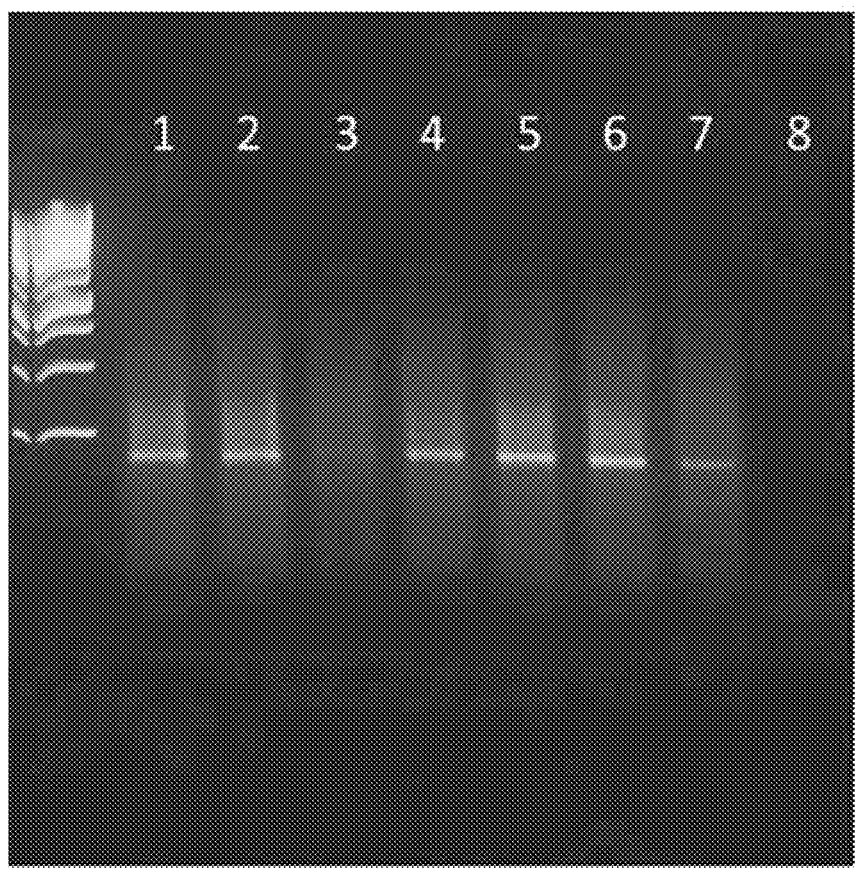
FIG. 15A-15B. Gel electrophoresis shows that conventional PCR retains only 25% efficiency when 1 mM $Ca^{2+}$ is added (15A). At 100 µM, 75% efficiency is achieved. No significant changes are observed at 10 µM or lower (15B).
Figure 15B:
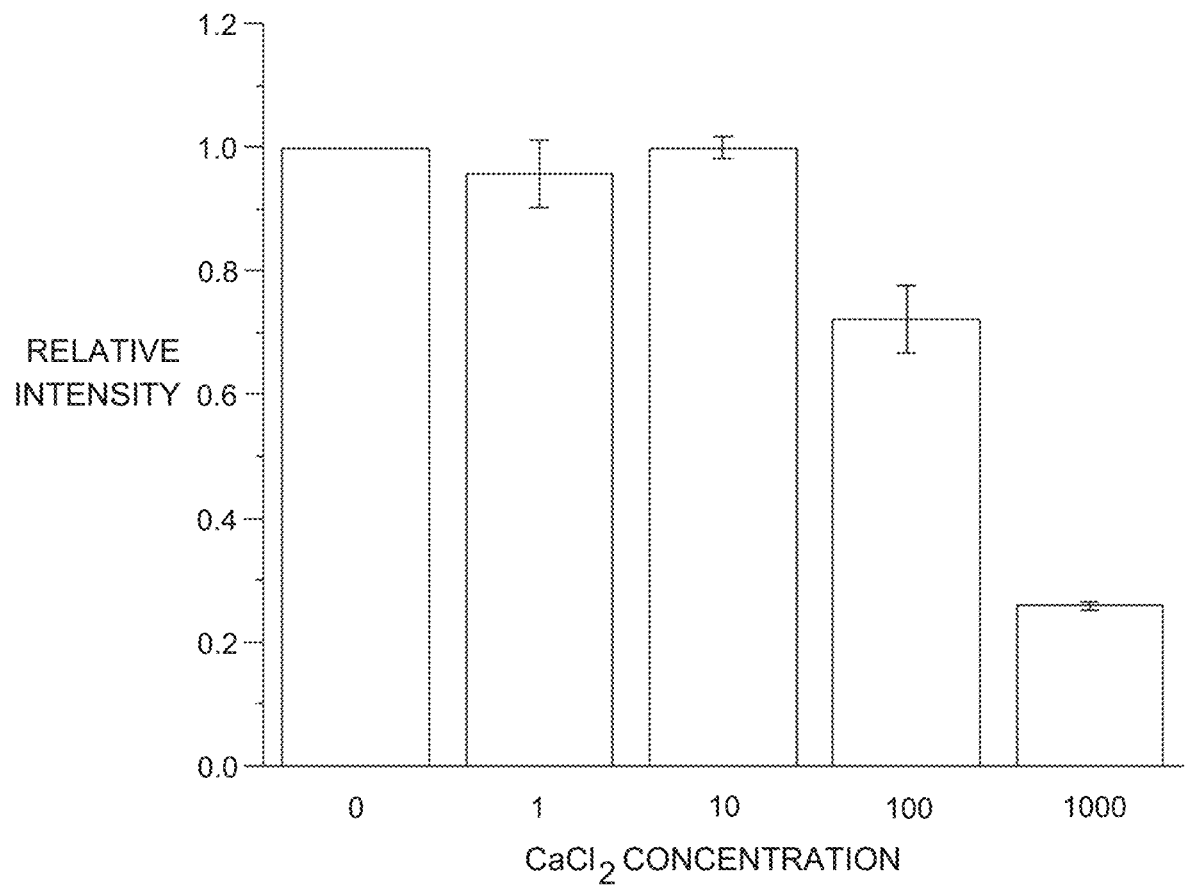

The presence of inhibitors inside body fluids contributes to decrease in PCR efficiency and accuracy and consequently make sample pretreatment a necessary step. Calcium ion ($Ca^{2+}$) is one of the most abundant ions in human blood with concentration of about 1 mM. It has been documented that the presence of Ca' at high concentration inhibits the PCR reaction. A comparison between conventional PCR followed by gel electrophoresis analysis and AC spray digital PCR was performed. For the comparison, a final concentration of up to 1 mM $CaCl_2$ was introduced into the PCR mix and conventional PCR was performed. As shown in FIG. 15A and FIG. 15B, the band intensity for an amplicon drops to about 75% of positive control with 100 µM of $CaCl_2$ and 25% with 1 mM $CaCl_2$. For the AC spray digital PCR platform, PCR efficiency drops only to about 50% of positive control at 1 mM $CaCl_2$ concentration. At 100 µM PCR amplification result is similar to that of positive control. These results obtained for the disclosed digital PCR system demonstrate that it is possible to offset inhibition more effectively than conventional PCR, but requires further optimization.

Example 6. Testing Real Biological Samples

Experiments were conducted in samples with defined conditions, and purified DNA used for PCR. Therefore, this disclosure can be used for the testing of human urine due to its relative simplicity in content and its low protein concentration. More complicated biological samples such as blood serum can be used with further refinements to determine which purification steps used in conventional PCR techniques can be omitted to increase throughput.

Example 7. One Step Reverse Transcription in Droplets

Amplification and quantification of miRNA requires conversion of miRNA to cDNA using reverse transcription. Thus, a method to spray the reagents and enzymes needed for both reverse transpiration and PCR at the same time could be possible by the techniques described in this disclosure. Since smaller and more numerous droplets may be required for optimization the present disclosure can provide for adjustment of those parameters.

Example 8. Amplification and Detection of Multiple Targets

The present disclosure allows for two methods useful for the detection of multiple targets. The first method uses molecular beacons with attached reporters that have different fluorescent colors. The advantage of this method is that all reagents can be added into the same sample with no further sample partitioning required. Due short sequences in miRNA, nonspecific amplification may be accomplished more easily than, for example, the longer sequences in RNA.

Alternatively, the samples can be partitioned into different portions, depending on the number of miRNA of interest. For each partition, only 1 specific set of primers are added. Each partition can enter the spraying chamber at a different time, which can then be recorded by the detection unit. The advantage of this method is that nonspecific interactions from multiple sets of primers will be minimized. Since the fluorescent reporter can be identical for all partitions (intercalating dye that binds to double stranded DNA), the cost can be minimized. The concentration of the miRNA can be optimized so sensitivity is not affected by overly scarce miRNA.

Example 9. Sample Testing Against Cell Media, Spiked Samples and Clinical Samples This disclosure can also be useful for spiked blood and urine samples, assays for cancer cell media, and clinical samples.

CONCLUSIONS

MicroRNA quantification and profiling shows very good promise for the diagnosis of early stage cancer due to its early release and stability inside human body fluids, making it the ideal target for liquid biopsy. However, a large dynamic range and a low limit of detection must be achieved by digital PCR for quantification to be accurate. A high throughput is necessary for the assay to be performed in a reasonable amount of time of 30 minutes to 1 hour per sample, including any necessary pretreatment. The droplet size must also reach the ideal number of $p=10^{10}$ to fully suppress inhibition and cross-talk. The current flow focusing and T-junction technologies cannot produce this large number of droplets, they often encapsulate more than one template and use Poisson statistics to estimate the original template number.

The disclosed AC electrospray digital PCR platform does not use hydrodynamic forces to pinch off the droplets, and can generate drops ranging from 1-5 µm in size, which is 10-1000 times smaller than the current technology. It can also generate droplets at a rate of 1 million droplets per second, which is more than 30 times faster than that of currently available commercial products. Thus, reaching the ideal number of $10^{10}$ droplets in less than 1/300 of the time can reduce or eliminate the necessity of sample dilution or pretreatment. The smaller droplets also increase the dynamic range by 3 orders of magnitude. This disclosure demonstrates that PCR viable droplets can be generated by AC electrospray. Furthermore, fluorescent droplets prepared by the disclosed techniques can be identified and counted. While only about 70% of theoretical yield is achieved, optimization of the PCR solution, spray parameters, PCR conditions, and the detection chip can be made to allow for more accurate quantification.

While specific embodiments have been described above with reference to the disclosed embodiments and examples, such embodiments are only illustrative and do not limit the scope of the invention. Changes and modifications can be made in accordance with ordinary skill in the art without departing from the invention in its broader aspects as defined in the following claims.

All publications, patents, and patent documents are incorporated by reference herein, as though individually incorporated by reference. No limitations inconsistent with this disclosure are to be understood therefrom. The invention has been described with reference to various specific and preferred embodiments and techniques. However, it should be understood that many variations and modifications may be made while remaining within the spirit and scope of the invention.

What is claimed is:

1. An alternating current droplet generator comprising:
   a) an electrospray emitter having a conical end and an orifice at the conical end, and a conduit to the orifice for a pressurized fluid, wherein the emitter can generate liquid droplets from the pressurized fluid at the orifice by an alternating current;
   b) an alternating current electrode configured to provide the alternating current;
   c) a droplet suspending medium wherein the medium comprises a carrier oil; and
   d) a droplet chamber comprising the medium, one or more inlets for the electrospray emitter and the medium, wherein the conical end of the emitter is at least partially inserted into the chamber, and the conical end is immersed in the medium;
   wherein more than 100 monodispersed liquid droplets per second can be produced from the pressurized fluid by the alternating current droplet generator in the droplet suspending medium to form an emulsion.

2. The apparatus of claim 1 wherein the electrospray emitter comprises glass, the alternating current electrode is internal to the electrospray emitter, and the droplet chamber comprises a counter electrode.

3. The apparatus of claim 1 wherein the conduit comprises the pressurized fluid, the pressurized fluid comprises a polymerase chain reaction (PCR) buffer, and the carrier oil is a mineral oil, a fluorinated oil, a silicone oil, or a combination thereof.

4. A droplet digital polymerase chain reaction (PCR) apparatus comprising:
   a) the alternating current droplet generator of claim 1;
   b) a capillary for a pressurized fluid sample comprising template molecules to flow from the capillary to the conduit of the electrospray emitter;
   c) a PCR thermal cycler, having an optional Peltier heater, configured to receive an emulsion of a fluid sample from the droplet chamber; and
   d) a detector;
   wherein a sufficient number of liquid droplets are generated from a pressurized fluid sample to achieve a binary distribution of template molecules among the droplets, when an alternating current is applied to the pressurized fluid sample comprising template molecules at the electrospray emitter, and the distribution of zero or one template molecule per droplet is independent of the template number in the fluid sample.

5. The apparatus of claim 4 wherein the electrospray emitter comprises glass with an internal alternating current electrode, or the electrospray emitter comprises a conductive metal in contact with an alternating current electrode.

6. The apparatus of claim 4 wherein an emulsion can flow through the PCR thermal cycler, wherein the PCR thermal cycler comprises a) a serpentine channel, or b) a chip chamber for batch PCR.

7. The apparatus of claim 4 wherein the detector comprises a fluorescence detector, a radioactive detector, a two-dimensional detector, a three-dimensional detector, or a combination thereof.

8. The apparatus of claim 4 wherein the apparatus has a dynamic range of at least 4 orders of magnitude and a sensitivity to detect a polynucleotide of less than about 500 nucleic acid bases (NABs), less than about 100 NABs, less than about 50 NABs, or less than about 25 NABs.

9. A method for producing liquid droplets comprising:
   a) applying an alternating current electric field to the electro spray emitter of claim 1;
   b) introducing a fluid into the emitter; and
   c) generating an electrospray by the emitter from the fluid at a rate of more than 100 liquid droplets per second in a droplet suspending medium to form a stable emulsion;
   wherein the electrospray produces monodispersed liquid droplets having a diameter ranging from about 0.1 micrometers to about 1000 micrometers in the droplet suspending medium.

10. The method of claim 9 wherein the frequency of the alternating current ranges from about 1 kilohertz to about 1000 kilohertz.

11. The method of claim 10 wherein the potential of the alternating current ranges from about 0.01 kilovolts to about 100 kilovolts.

12. The method of claim 9 wherein the fluid comprises a template molecule, one or more PCR reagents, and water.

13. The method of claim 12 wherein a) the fluid further comprises a surfactant, b) the carrier oil further comprises a surfactant, or c) both the fluid and the carrier oil further comprise a surfactant.

14. The method of claim 12 wherein the fluid is flowing at rate of about 10 microliters per minute to about 100 microliters per minute.

15. The method of claim 9 wherein the droplet suspending medium comprises a flowing carrier oil.

16. The method of claim 15 wherein the carrier oil is a mineral oil, a fluorinated oil, a silicone oil, or a combination thereof.

17. The method of claim 9 wherein the fluid comprises one or more biological substances.

18. The method of claim 9 wherein the droplet suspending medium substantially comprises flowing water.

19. A method for performing droplet digital polymerase chain reaction (PCR) comprising:
   a) applying an alternating current electric field to the electrospray emitter of claim 1;
   b) introducing a fluid into the emitter, wherein the fluid comprises one or more template molecules and PCR reagents;
   c) generating an electrospray by the emitter from the fluid at a rate of more than 100 liquid droplets per second in a droplet suspending medium to form a stable emulsion;
   d) amplifying an amplicon of one or more template molecules in a PCR thermal cycler; and
   e) detecting the amplicons;
   wherein the electrospray produces monodispersed liquid droplets having a diameter ranging from about 0.1 micrometers to about 1000 micrometers in the droplet suspending medium.

20. An alternating current droplet generator comprising:
   a) a glass electrospray emitter having a conical end, an orifice at the conical end, and a conduit to the orifice;
   b) an alternating current electrode internal to the electrospray emitter;
   c) a droplet suspending carrier oil; and
   d) a droplet chamber comprising the oil, a counter electrode, one or more inlets for the electrospray emitter and the oil, wherein the conical end of the emitter is at least partially inserted into the chamber and the conical end is immersed in the oil.

* * * * *